US012714583B2

(12) United States Patent
Moor

(10) Patent No.: US 12,714,583 B2
(45) Date of Patent: Aug. 25, 2026

(54) EXPANDABLE TUBE FOR DEPLOYMENT WITHIN A BLOOD VESSEL

(71) Applicant: Oxford Endovascular Ltd., Oxford (GB)

(72) Inventor: Andrew Moor, Northleach (GB)

(73) Assignee: Oxford Endovascular Ltd., Oxford (GB)

( * ) Notice: Subject to any disclaimer, the term of this patent is extended or adjusted under 35 U.S.C. 154(b) by 947 days.

(21) Appl. No.: 17/932,030

(22) Filed: Sep. 14, 2022

(65) Prior Publication Data

US 2023/0031643 A1 Feb. 2, 2023

Related U.S. Application Data

(63) Continuation of application No. PCT/GB2021/050609, filed on Mar. 11, 2021.

(30) Foreign Application Priority Data

May 20, 2020 (GB) ..................................... 2007488

(51) Int. Cl.

*A61F 2/852* (2013.01)
*A61F 2/90* (2013.01)
*A61F 2/915* (2013.01)
*A61F 2/82* (2013.01)

(52) U.S. Cl.

CPC ................ *A61F 2/852* (2013.01); *A61F 2/90* (2013.01); *A61F 2/915* (2013.01); *A61F 2002/823* (2013.01); *A61F 2002/825* (2013.01); *A61F 2210/0014* (2013.01); *A61F 2210/0066* (2013.01); *A61F 2250/001* (2013.01); *A61F 2250/0098* (2013.01)

(58) Field of Classification Search

CPC ................................. A61F 2/852; A61F 2/885

See application file for complete search history.

(56) References Cited

U.S. PATENT DOCUMENTS 10,076,428 B2 9/2018 Gorochow
2007/0016283 A1 1/2007 Greenhalgh et al.
2007/0073383 A1 * 3/2007 Yip .......................... A61F 2/90 623/1.42

(Continued)

FOREIGN PATENT DOCUMENTS

CA 2887189 4/2008
CN 104487024 4/2015

(Continued)

*Primary Examiner* — Rebecca S Preston

(74) *Attorney, Agent, or Firm* — Levine Bagade Han LLP

(57) ABSTRACT

There is provided an expandable tube for deployment within a blood vessel, the expandable tube being reversibly switchable from a radially contracted and longitudinally expanded state to a radially expanded and longitudinally contracted state, the expandable tube comprising a first frame comprising braided filament, and a second frame connected to the first frame and overlapping with the first frame in the radial direction, the second frame comprising a network of non-overlapping elements, the non-overlapping elements being non-overlapping with respect to each other in the radial direction, wherein the network of non-overlapping elements has an interconnected structure comprising a plurality of sub-units that repeat in the longitudinal direction.

24 Claims, 12 Drawing Sheets

(56) References Cited

U.S. PATENT DOCUMENTS

2010/0152834 A1 6/2010 Hannes et al.
2013/0245745 A1* 9/2013 Vong ........................ A61F 2/852 623/1.22
2013/0345739 A1* 12/2013 Brady ............ A61B 17/320725 606/200
2014/0288634 A1* 9/2014 Shalev .................... A61F 2/915 623/1.16
2014/0309723 A1 10/2014 Bar et al.
2016/0158038 A1 6/2016 Teitelbaum
2018/0055665 A1 3/2018 Gorochow
2018/0085128 A1 3/2018 Bellomo
2018/0311056 A1 11/2018 Pung et al.
2019/0133795 A1* 5/2019 Choubey ................... A61F 2/90
2020/0008962 A1 1/2020 Keeble

FOREIGN PATENT DOCUMENTS

CN 107970082 5/2018
CN 110691569 1/2020
EP 2684545 1/2014
EP 3311782 4/2018
IL 198665 2/2014
JP 2018-064943 4/2018
WO WO 2001/074272 10/2001
WO WO 2013/138789 9/2013

* cited by examiner

EXPANDABLE TUBE FOR DEPLOYMENT WITHIN A BLOOD VESSEL

CROSS-REFERENCE TO RELATED APPLICATIONS

This application is a continuation of International Patent Application Number PCT/GB2021/050609 filed Mar. 11, 2021, which claims the benefit of priority to GB 2007488.6 filed May 20, 2020, the contents of which are incorporated herein by reference in their entireties.

TECHNICAL FIELD

The present invention relates to an expandable tube for deployment within a blood vessel, particularly for use in redirecting blood flow away from an aneurismal sac.

BACKGROUND

An intracranial aneurysm is a weak region in the wall of an artery in the brain, where dilation or ballooning of the arterial wall may occur. Histologically, decreases in the tunica media, the middle muscular layer of the artery, and the internal elastic lamina cause structural defects. These defects, combined with hemodynamic factors, lead to aneurismal out-pouchings. Intracranial aneurysms are quite common diseases with a prevalence ranging from one to five percent among adult population according to autopsy studies. In the US alone, ten to twelve million people may have intracranial aneurysms.

Current methods for treating intracranial aneurysms include surgical clipping and endovascular coiling. In the surgical clipping method, the skull of the patient is opened, and a surgical clip is placed across the neck of the aneurysm to stop blood from flowing into the aneurysm sac. The risk of this method is relatively high, especially for elderly or medically complicated patients. Endovascular coiling is a less invasive method involving placement of one or more coils, delivered through a catheter, into the aneurysm until the sac of the aneurysm is completely packed with coils. It helps to trigger a thrombus inside the aneurysm. Although endovascular coiling is deemed to be safer than surgical clipping, it has its own limitations. First, after the aneurysm is filled with the coils, it will remain its original size. As a result, the pressure on the surrounding tissue exerted by the aneurysm will not be removed. Second, this procedure is not very effective for wide-necked aneurysms, where the coil is likely to protrude into the parent vessels. This problem may be mitigated by using a stent in combination with coiling embolization, but the procedure is difficult and time-consuming.

Using an expandable tube, sometimes referred to as a stent, alone to treat the aneurysm is a promising way to avoid the problems stated above. In this method, an expandable tube with an area of relatively low porosity is placed across the aneurysm neck in such a way as to redirect blood flow away from the sac and trigger formation of a thrombus within the aneurysm. Because the aneurysm solidifies naturally on itself, there is less danger of its rupture. Furthermore, because no coil is involved in this method, the aneurysm will gradually shrink as the thrombus is absorbed. Consequently, the pressure applied on the surrounding tissue can be removed. It is difficult, however, to manufacture an expandable tube having optimal characteristics for this application. The expandable tube has to be flexible enough to pass through and adapt to the shape of the very tortuous blood vessels in the brain while at the same time providing sufficiently low porosity to redirect blood flow away from the aneurysm to an adequate extent.

A known type of expandable tube is formed from braided filaments, for example of wire. The filaments are braided together to form a mesh tube. Expandable tubes of this type can be radially contracted and longitudinally expanded inside a catheter for placement into blood vessels. When in the correct position over the neck of the aneurysm, the expandable tube is deployed from inside the catheter, whereupon it expands radially and contracts longitudinally so that it becomes lodged in the blood vessel and occludes the blood flow in and out of the aneurysm. However, a problem with braided filament expandable tubes is that the large number of contact points between filaments in the braided structure create friction.

Additionally, each filament is free to move relative to other intersecting filaments resulting in poor radial outward force. This can cause braided filament expandable tubes to radially expand slowly and inconsistently on deployment from the catheter, thereby making correct placement of the expandable tube relative to the neck of the aneurysm more difficult and less reliable.

Another existing type of expandable tube is formed of a network of interconnecting and non-overlapping elements. This may be formed, for example, by laser cutting from a narrow tube of a material such as a shape-memory alloy. These laser-cut tubes have the advantage that there are no points of contact between braided filaments to cause friction, and their deployment can be more consistent. However, it can be difficult to design tubes of this type that have sufficiently low porosity to adequately occlude an aneurysm.

SUMMARY

It is an object of the invention to provide an expandable tube for deployment within a blood vessel that has improved performance, particularly with regard to the deployment of the expandable tube.

According to an aspect of the invention, there is provided an expandable tube for deployment within a blood vessel, the expandable tube being reversibly switchable from a radially contracted and longitudinally expanded state to a radially expanded and longitudinally contracted state, the expandable tube comprising a first frame comprising braided filament, and a second frame connected to the first frame and overlapping with the first frame in the radial direction, the second frame comprising a network of non-overlapping elements, the non-overlapping elements being non-overlapping with respect to each other in the radial direction, wherein the network of non-overlapping elements has an interconnected structure comprising a plurality of sub-units that repeat in the longitudinal direction.

By using an expandable tube with a hybrid structure including a frame of braided filaments and a frame comprising a network of non-overlapping elements, it is possible to combine their respective advantages of consistent deployment and low porosity. The frame comprising non-overlapping elements provides additional force to expand the braided frame. Combining the two types of frame requires careful design of the two tubes, so that their differing expansion properties do not interfere with the correct operation of the two frames. Additionally, the advantageous expansion properties of the frame comprising non-overlapping elements allows the frame comprising braided filaments to be made using filaments having a smaller diameter. This enables the frame of braided filaments to be comprised of additional filaments while remaining compatible with the necessary accessory devices (e.g., a microcatheter used for delivery of the expandable tube into a blood vessel). A higher filament count reduces the size of individual pores between the filaments in the wall of the expandable tube, which is associated with greater flow reduction within the aneurysm sac and quicker reendothelialization across the neck of the aneurysm.

In an embodiment, the network of non-overlapping elements comprises a plurality of longitudinally and/or circumferentially deformable elements. In an embodiment, the network of non-overlapping elements comprises a plurality of longitudinally deformable elements for providing longitudinal expansion and contraction of the second frame, and a plurality of circumferentially deformable elements for providing radial expansion and contraction of the second frame. This allows the frame to change both its radial and longitudinal dimensions, which can allow the expansion/contraction ratio of the tube to be increased. This allows the tube to be more easily inserted into a microcatheter for deployment.

In an embodiment, the longitudinally deformable elements are configured to be expanded or contracted longitudinally substantially without any substantial change in the shape of the circumferentially deformable elements. In an embodiment, the circumferentially deformable elements are configured to be expanded or contracted circumferentially substantially without any substantial change in the shape of the longitudinally deformable elements. By designing the longitudinally deformable elements and the circumferentially deformable elements such that they can expand and contract substantially independently, it is easier to design the second frame such that its expansion properties match those of the first frame.

In an embodiment, the second frame is configured to drive the expandable tube from the radially contracted and longitudinally expanded state to the radially expanded and longitudinally contracted state. Using the second frame to drive the expansion of the first frame helps the tube to deployment more consistently and reliably, thereby reducing the likelihood of a failed deployment.

In an embodiment, the second frame is configured to drive the expandable tube from the radially contracted and longitudinally expanded state to the radially expanded and longitudinally contracted state by exerting a force on the first frame in a radial direction. Exerting a force in the radial direction means that the first frame will rapidly expand to its full diameter when released from a deployment catheter, so that it can more easily be placed correctly.

In an embodiment, the network of non-overlapping elements is integrally formed. This reduces the complexity of the manufacturing process by removing the need to join elements of the network. It will also reduce defects or irregularities in the surface of the second frame due to joins between elements.

In an embodiment, the second frame comprises a shape memory alloy material, preferably nitinol. Shape memory alloys are a convenient choice of material, as they can be designed to revert to a desired shape when released from constraint, thereby removing the need to exert external forces on the tube to cause them to radially expand.

In an embodiment the second frame has a porosity of at least 70%. By having a relatively high porosity of the second frame, the first frame is the main determiner of the porosity of the expandable tube, simplifying design of the overall properties of the expandable tube.

In an embodiment, the length of the second frame is at least 50% of the length of the first frame. In an embodiment, the second frame overlaps with the first frame over at least 50% of the length of the expandable tube. These requirements ensure that the second frame is able to interact with the first frame over a majority of its length, thereby creating a uniform behavior of the expandable tube.

In an embodiment, the second frame is connected to the first frame at least at one end of the second frame. Connecting the two frames together ensures that they do not move relative to one another, and the expandable tube behaves consistently and predictably.

In an embodiment, the second frame is further connected to the first frame at one or more points along the length of the second frame. This means that the interaction of the first frame and second frame is uniform along the length of the expandable tube, and not only constrained at the ends of the expandable tube.

In an embodiment, the second frame is connected to the first frame by at least one of welding, crimping, an adhesive, or encapsulation. These are particularly convenient joining methods where the first frame is formed of braided filament.

In an embodiment, the second frame comprises a plurality of filament-receiving apertures, one or more connecting filaments are woven into the first frame, and each connecting filament passes through one or more of the filament-receiving apertures. Using connecting filaments reduces the profile of the joining between the first and second frames compared to other methods such as crimping or welding, making the surface of the expandable tube more uniform.

In an embodiment, the connecting filaments comprise filaments of the first frame. This means no additional filaments are added, keeping the dimensions of the expandable tube the same as if no connecting filaments were present.

In an embodiment, one or more radiopaque markers are attached to one or more of the connecting filaments. The connecting filaments are a convenient attachment point for radiopaque markers that improve the visibility of the expandable tube during deployment.

In an embodiment, the plurality of filament-receiving apertures comprises filament-receiving apertures in a longitudinal end region of the second frame. This secures the overall length of the two frames together.

In an embodiment, the plurality of filament-receiving apertures comprises filament-receiving apertures spaced along the length of the second frame. Including further apertures spaced along the second frame improves the attachment of the first and second frames to one another, reducing the chance of the two frames separating.

In an embodiment, the second frame is positioned within the first frame. Having the braided filament on the outside of the expandable tube means that a uniform sheath is provided along the length of the expandable tube. This provides a greater radial expansion force on the first frame than if the second frame were provided outside of the first frame, thereby further promoting proper deployment of the expandable tube.

In an embodiment, a radius of the second frame in an unconstrained state in which the second frame is not connected to the first frame and the second frame is radially expanded and longitudinally contracted is greater than a radius of the first frame in an unconstrained state in which the first frame is not connected to the second frame and the first frame is radially expanded and longitudinally contracted. Oversizing the second frame, such that its unconstrained radius is larger than that of the first frame, helps to ensure the second frame is able to drive deployment of the expandable tube and minimize the risk of radial separation between the two frames, particularly when deployed in tortuous anatomy. This also means fewer fixation points are required to join the two frames together securely.

In an embodiment, a first elongation ratio of the first frame is within 25% of a second elongation ratio of the second frame, the first elongation ratio being a ratio between the length of the first frame in an unconstrained state in which the first frame is not connected to the second frame and the first frame is radially expanded and longitudinally contracted and the length of the first frame in the radially contracted and longitudinally expanded state, and the second elongation ratio being a ratio between the length of the second frame in an unconstrained state in which the second frame is not connected to the first frame and the second frame is radially expanded and longitudinally contracted and the length of the second frame in the radially contracted and longitudinally expanded state. Previous designs of expandable tubes comprising braided filaments have included expansion rings at one or both ends of the expandable tube to promote proper deployment of the end of the braided tube. However, increasing the length of the expansion rings relative to the braided stent to promote proper deployment over the full length is challenging because the expansion characteristic of the two types of frame are different. Matching the elongation ratios ensures that no creasing or buckling of the first frame or the second frame will occur when deploying the expandable tube, thereby reducing the chance of complications from the deployment. This further permits the second frame to be made longer in relation to the first frame, and further improve the consistency of deployment of the expandable tube.

In an embodiment, the network of non-overlapping elements comprises a plurality of longitudinally deformable elements for providing longitudinal expansion and contraction of the second frame, each sub-unit of the network of non-overlapping elements has a first length in the longitudinal direction in the unconstrained state in which the second frame is not connected to the first frame and the second frame is radially expanded and longitudinally contracted state, and a ratio between the first length and a path length along each longitudinally deformable element is within 25% of the first elongation ratio. Choosing the path length along the longitudinally deformable elements correctly will determine the longitudinal expansion of the second frame such that it matches to the first elongation ratio of the first frame.

In an embodiment, the first frame comprises a shape memory alloy material, preferably nitinol. Shape memory alloys are a convenient choice of material, as they can be designed to revert to a desired shape when released from constraint, thereby removing the need to exert external forces on the tube to cause them to radially expand.

In an embodiment, when the expandable tube is positioned in use over the opening to an aneurismal sac in the radially expanded and longitudinally contracted state, the first frame has a porosity such as to redirect blood flow away from the aneurismal sac and thereby promote thrombus formation in the aneurismal sac. This ensures the expandable tube is operative in causing thrombus formation in the aneurysm.

In an embodiment, the first frame has a porosity of at most 90% in the radially expanded and longitudinally contracted state of the expandable tube. Limiting the porosity of the first frame reduces the porosity of the expandable tube such that it can cause thrombus formation in an aneurysm.

In an embodiment, the first frame comprises at least 48 filaments. Higher filament count helps to increase pore density, which improves the ability of the expandable tube to occlude aneurysms.

In an embodiment, the filaments of the first frame have a diameter of at most 30 μm. Smaller diameter filaments allow the filament count to be increased while maintaining compatibility with a suitably sized microcatheter.

In an embodiment, the first frame has a pore density of at least 30 pores/mm$^2$. Higher pore density improves the ability of the expandable tube to occlude aneurysms, and promotes endothelialization of the tube.

In an embodiment, in the radially contracted and longitudinally expanded state, the expandable tube has a maximum dimension in the radial direction that is at least 30% smaller than the maximum dimension in the radial direction of the expandable tube in the radially expanded and longitudinally contracted state. This will allow for sufficient compression of the expandable tube such that it can be inserted into a catheter for deployment.

In an embodiment, an elongation of the expandable tube in the longitudinal direction caused by the switching from the radially expanded and longitudinally contracted state to the radially contracted and longitudinally expanded state is at least 10%. Providing for longitudinal expansion and contraction increases the extent to which the expandable tube is able to expand and contract radially.

In an embodiment, in the radially contracted and longitudinally expanded state, a maximum dimension in the radial direction of the expandable tube is such that the expandable tube can be inserted into a catheter having an inner diameter of at most 1.0 mm. This size of catheter is widely available and routinely used for treatment of brain aneurysms, and so compatibility with this catheter size is desirable.

BRIEF DESCRIPTION OF THE DRAWINGS

Embodiments of the invention will now be described, by way of example only, with reference to the accompanying drawings in which corresponding reference symbols indicate corresponding parts, and in which.

DETAILED DESCRIPTION

The present disclosure provides expandable tubes suitable for deployment within a blood vessel. The expandable tubes, which may also be known as stents, are suitable for use in methods for the treatment of aneurysms. In particular, the designs herein are suitable use in methods for the treatments of cerebral aneurysms, where the blood vessels in which the expandable tubes must be deployed are narrow and tortuous.

Figure 1:
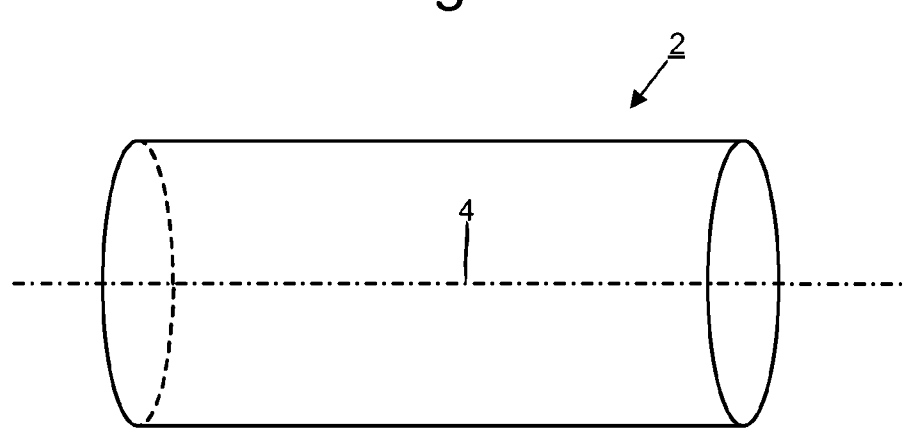
FIG. 1 is a schematic of an expandable tube in the radially expanded and longitudinally contracted state.
Figure 2:
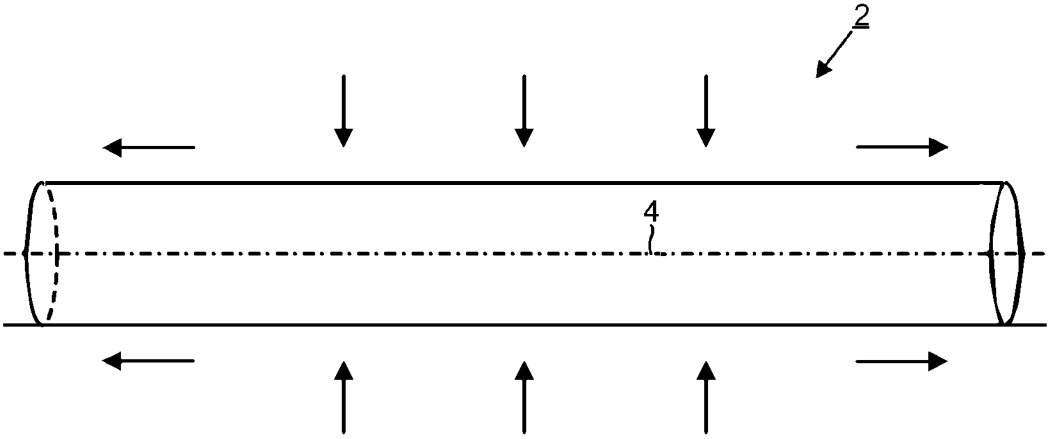
FIG. 2 is a schematic of an expandable tube in the radially contracted and longitudinally expanded state.

FIG. 1 depicts the outer geometry of an expandable tube 2 in a radially expanded and longitudinally contracted state. FIG. 2 depicts the outer geometry of the expandable tube 2 in a radially contracted and longitudinally expanded state. The expandable tube 2 is reversibly switchable from the radially contracted and longitudinally expanded state shown in FIG. 2 to the radially expanded and longitudinally contracted state shown in FIG. 1. As will be discussed further, the expandable tube 2 comprises a first frame 10 comprising braided filament, and a second frame 12 comprising a network of non-overlapping elements.

The expandable tube 2 is elongate relative to an axis of elongation 4. The expandable tube 2 may be cylindrical for example. When the expandable tube 2 is cylindrical, the maximum lateral dimension is the same at all positions and angles (i.e., it is equal to the diameter). When the expandable tube 2 is not cylindrical the maximum lateral dimension may be different at different positions and/or angles. The maximum lateral dimension defines the minimum interior diameter of a cylindrical tube (e.g., a delivery catheter) that the frame could be inserted into.

In the radially contracted state, the expandable tube 2 is substantially narrower than in the radially expanded state. Preferably in the radially contracted and longitudinally expanded state, the expandable tube 2 has a maximum dimension in the radial direction that is at least 30% smaller than the maximum dimension in the radial direction of the expandable tube 2 in the radially expanded and longitudinally contracted state, more preferably at least 50% smaller. Radially contracting the expandable tube 2 allows the expandable tube 2 to be inserted into a narrower delivery catheter for deployment at the site of interest. It is generally desirable for the delivery catheter to be as narrow as possible. This is particularly the case where access to a deployment site requires navigation of tortuous regions of vasculature. This may often be the case, for example, when treating a cerebral aneurysm.

In the discussion below it is understood that the term porosity, p, refers to the ratio of the surface area of open regions to the total external surface area occupied by the expandable tube 2, a portion of the expandable tube 2 that is being described, or a frame of the expandable tube 2 (which will be discussed further below). The total external surface area is the sum of the surface area of the open regions and the surface area of the regions occupied by the material of the expandable tube 2 or frame. When the expandable tube 2 or frame is cylindrical, the total external surface area is simply $2\pi.R.L$, where R is the radius of the cylinder and L is the length of the cylinder.

Consider the second frame 12 of the expandable tube 2, which comprises elements that are not allowed to overlap with each other in the radial direction. The second frame 12 has a porosity p in the fully radially expanded state. If the radius and length of the second frame 12 in the fully radially expanded state are $R_0$ and $L_0$, respectively, the minimum radius $R_{min}$ that the second frame 12 can achieve in the radially contracted state, defined by the state in which the porosity becomes zero, is governed by $$R_{min} = \frac{(1-\rho)L_0}{L_1}R_0$$

where $L_1$ is the length of the second frame 12 in the radially contracted state.

This relationship illustrates that if the length of the second frame 12 is not allowed to change to any significant extent, the radius can only reduce by a factor of p. As p needs to be quite low (e.g., less than 90%, preferably less than 80%, at least in a low porosity region, such as a region intended for positioning in use over the opening to an aneurismal sac), this represents a significant limitation to the extent to which the second frame 12 can be narrowed for insertion into a delivery catheter. For example, if the porosity p of the second frame 12 is 20% and the length of the second frame 12 is not allowed to change during radial contraction, i.e., $L_1=L_0$, the second frame 12 can achieve only a maximum 20% reduction in radius. Permitting an increase in length is also important for a frame comprising braided filaments, such as the first frame 10. The first frame 10 is unable to reduce in radius if its length cannot change due to its braided structure, and the greater the increase in length that is possible, the greater the possible reduction in radius.

The provision of an expandable tube 2 with frames that can expand longitudinally when adopting the radially contracted state is based on this understanding and allows much greater reductions in radius to be achieved. For example, if the length is allowed to double, i.e., $L_1=2L_0$, the second frame 12 can achieve a 60% reduction in radius for a porosity of 20%. For this reason, an elongation of the expandable tube 2 (or of a frame which forms a part of the expandable tube 2) in the longitudinal direction caused by the switching from the radially expanded and longitudinally contracted state to the radially contracted and longitudinally expanded state is preferably at least 10%, more preferably at least 20%, most preferably at least 30%.

Figure 3:
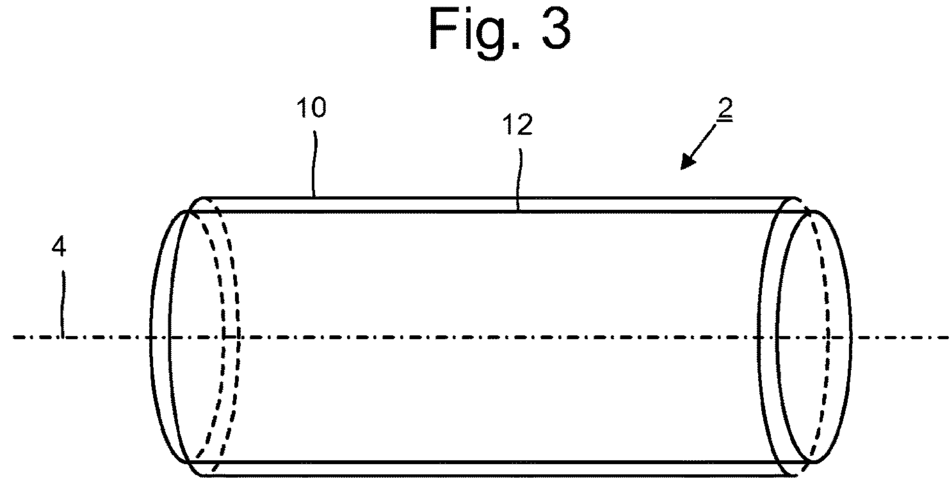
FIG. 3 is a schematic of an expandable tube comprising a first frame and a second frame in the radially expanded and longitudinally contracted state.
Figure 4:
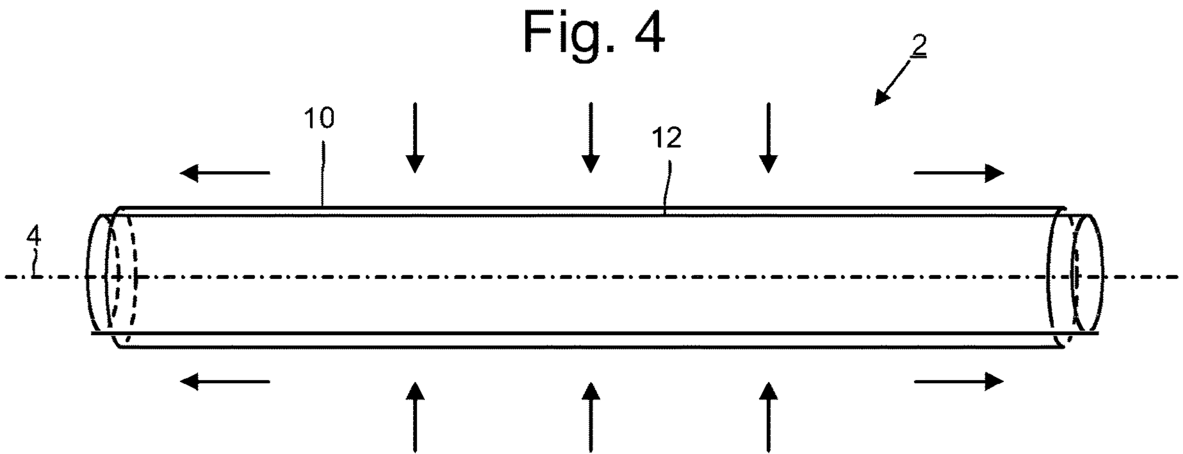
FIG. 4 is a schematic of an expandable tube comprising a first frame and a second frame in the radially contracted and longitudinally expanded state.
Figure 5:
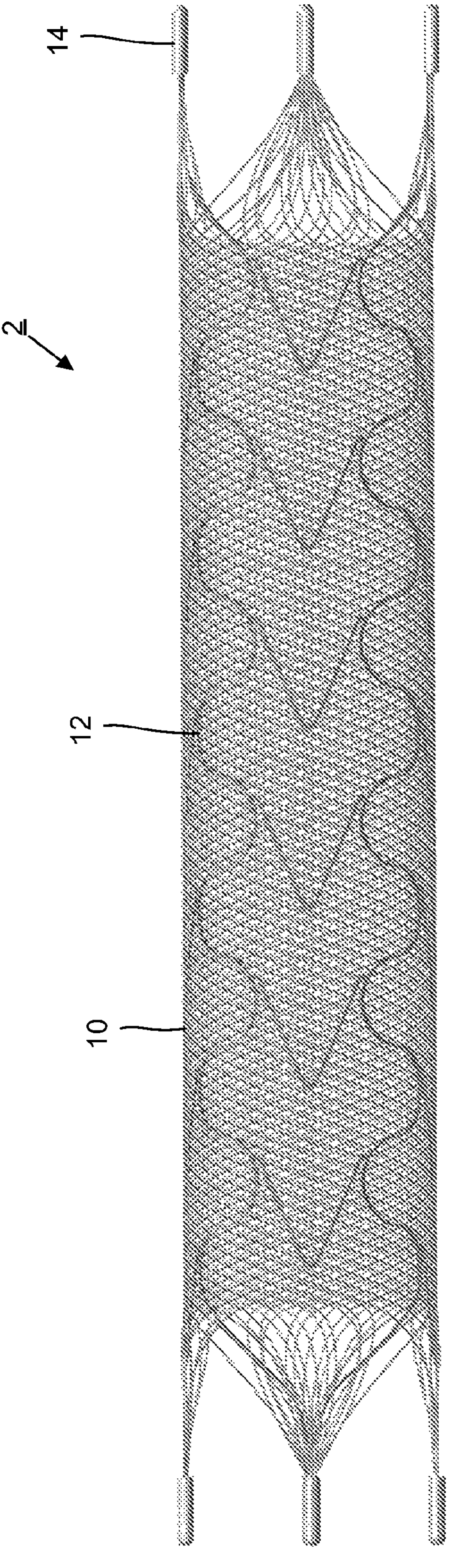
FIG. 5 shows an expandable tube comprising a first frame and a second frame, where the first frame is connected to the second frame at the ends of the first frame and second frame.

FIG. 3 shows further detail of the expandable tube 2 in the radially expanded and longitudinally contracted state. The expandable tube 2 comprises a first frame 10 comprising braided filament, and a second frame 12. FIG. 4 depicts the expandable tube 2 of FIG. 3 in the radially contracted and longitudinally expanded state. In FIG. 4, both the first frame 10 and the second frame 12 have contracted radially and expanded longitudinally relative to their states in FIG. 3. An example of an embodiment of the expandable tube 2 of FIGS. 3 and 4 is shown in FIG. 5. The braided filaments of the first frame 10 and the structure of the second frame 12 can be clearly seen.

Figure 6:
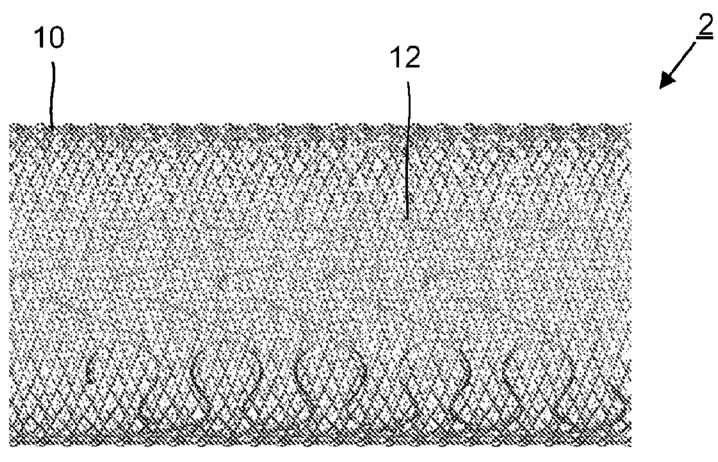
FIG. 6 shows an expandable tube comprising a first frame and a second frame in the radially expanded and longitudinally contracted state.
Figure 7:
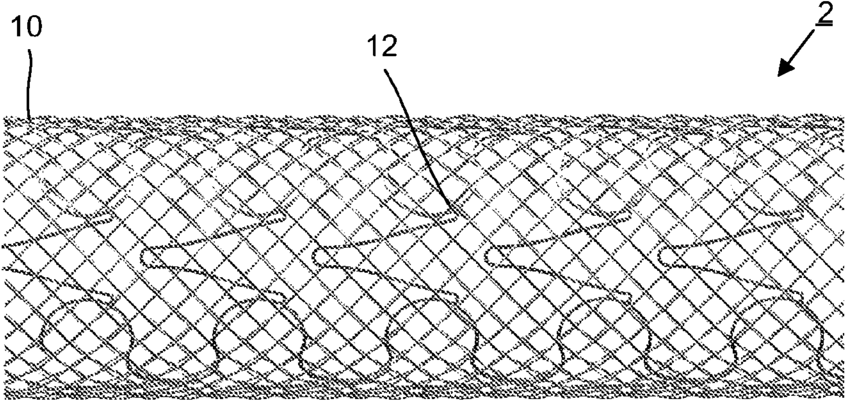
FIG. 7 shows an expandable tube comprising a first frame and a second frame in an intermediate state during expansion or contraction of the expandable tube.
Figure 8:
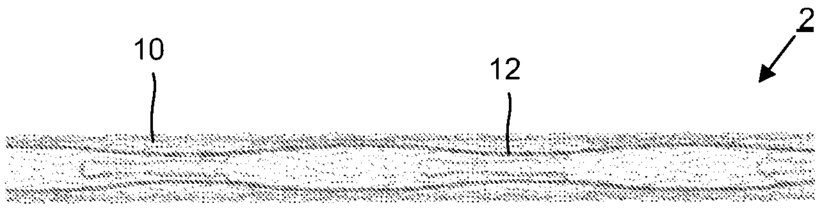
FIG. 8 shows an expandable tube comprising a first frame and a second frame in the radially contracted and longitudinally expanded state.

FIGS. 6 to 8 demonstrate the process by which the expandable tube 2 switches to the radially contracted and longitudinally expanded state shown in FIG. 3 from the radially expanded and longitudinally contracted state shown in FIG. 4. The spaces between the filaments of the first frame 10 shift from diamonds with their long axes oriented circumferentially to diamonds with their long axes oriented longitudinally. The elements of the second frame 12 contract circumferentially, and expand longitudinally. In the state shown in FIG. 6, the expandable tube 2 has its maximum diameter, such that it can engage the walls of a blood vessel in which it is deployed. In the intermediate state shown in FIG. 7, the porosity of the expandable tube 2 is maximal, because the spaces between filaments in the first frame 10 have their largest area. In the state shown in FIG. 8, the expandable tube 2 has its minimum diameter such that it can be inserted into a catheter for deployment into a blood vessel.

The first frame 10 comprises braided filament. The first frame 10 may comprise a large number of filaments braided together. As seen in FIG. 5, the first frame 10 comprises a plurality of helically-arranged filaments. The first frame 10 comprises filaments arranged in both right-handed helices and left-handed helices of equal diameter. In this way, the filaments of helices of opposing handedness overlap one another in the radial direction in order to form the braided structure of the first frame 10. An individual filament in a helix of a first handedness may alternately pass under and over the filaments of helices of the second handedness (different from the first) in order to form the braided structure (under and over being interpreted as respectively closer to and further from the axis of the expandable tube 2 in the radial direction). Other arrangements are also possible. For example, filaments in helices of the first handedness may pass alternately under and over pairs of filaments in helices of opposing handedness, or larger sets of filaments, such as three, four, or more filaments. Passing under and over multiple filaments of helices of opposing handedness may be advantageous in reducing the deformation of individual filaments, and reducing strain and friction between the filaments. However, passing under and over too many filaments at a time may reduce the integrity of the first frame 10.

The first frame 10, specifically the filaments of the first frame 10, may comprise a shape memory alloy material, preferably nitinol. Shape memory alloy material is advantageous in driving radial expansion of the first frame 10, as it can be configured to urge itself towards the radially expanded state. Alternatively, the first frame 10 may comprise polymer, or other biocompatible material. In some embodiments, the first frame 10 may be independently self-expanding. That is, the first frame 10 is configured to self-expand from a radially contracted and longitudinally expanded state to a radially expanded and longitudinally contracted state, even in a state in which the first frame 10 is not connected to the second frame 12.

The filaments of the first frame 10 may comprise a radiopaque material, for example platinum. In an embodiment, the filaments of the first frame 10 comprise a core of radiopaque material inside a covering of another material. The covering may be a shape memory alloy, preferably nitinol. For example, the filaments of the first frame 10 may comprise drawn-filled tube nitinol wire with a platinum core. Such embodiments allow the first frame 10 to be made radiopaque, which greatly improves the visibility of the expandable tube 2 during deployment, and improves the accuracy with which the expandable tube 2 can be deployed. The covering material may also be chosen to have improved biocompatibility relative to the radiopaque core. The covering material may also be chosen to have other advantageous properties, such as the self-expanding properties of shape-memory alloy.

An important characteristic of stents used to treat aneurysms is their pore density, i.e., the number of pores in the wall of the tube per unit area. Increased pore density is associated with greater flow reduction within the aneurysm sac and more rapid re-endothelialization of the stent by the blood vessel, both of which lead to better and more reliable patient outcomes. It has therefore been an aim of designers of stents for some time to increase pore density in stents.

With frames (such as the first frame 10) that are made from braided filament, pore density can be increased by using narrower filaments and increasing the filament count (the total number of filaments around the diameter of the frame). However, narrower filaments are less stiff, and frames made from narrow filaments have poor expansion properties. Therefore, attempts to improve pore density in braided frames by using narrower filaments typically compound the already non-ideal expansion properties of braided frames.

Increasing the filament count without reducing the filament diameter can provide some benefit without worsening the expansion properties, but will increase the diameter of the stent in its radially contracted state. This makes the stent incompatible with standard sizes of catheter used in deploying stents to treat intracranial aneurysms, which are widely available and well understood by medical practitioners. Therefore, the problem of improving pore density in stents without increasing the diameter of the stent in the radially contracted state has remained without a satisfactory solution for some time.

As will be discussed further below, in the present invention, the second frame 12 can expand more easily and consistently than the first frame 10. Consequently, the second frame 12 may be configured to drive the expandable tube 2 from the radially contracted and longitudinally expanded state to the radially expanded and longitudinally contracted state, i.e., such that the expansion properties of the expandable tube 2 are mainly determined by the second frame 12. The advantageous expansion properties of the second frame 12 allow the first frame 10 to be made using filaments having a narrower diameter, because the first frame 10 is not relied on to cause the expansion of the expandable tube 2. Using filaments of narrower diameter allows the filament count of the first frame 10 to be increased relative to conventional braided stents without requiring an increase in the diameter of the expandable tube 2 in the radially contracted and longitudinally expanded state.

In turn, this improves the pore density of the first frame 10, while still allowing the expandable tube 2 to be compatible with standard sizes of catheter that are widely available for deploying the expandable tube 2 to treat intracranial aneurysms. For example, in an embodiment, in the radially contracted and longitudinally expanded state, a maximum dimension in the radial direction of the expandable tube 2 is such that the expandable tube 2 can be inserted into a catheter having an inner diameter of at most 1.0 mm. Preferably a maximum dimension in the radial direction of the expandable tube 2 is such that the expandable tube 2 can be inserted into a catheter having an inner diameter of 0.69 mm (0.027 inches) or 0.53 mm (0.021 inches), or less.

In an embodiment, the first frame 10 comprises at least 48 filaments, preferably at least 64 filaments, more preferably at least 72 filaments, most preferably at least 96 filaments. In an embodiment, the filaments of the first frame 10 have a diameter of at most 30 μm, preferably at most 25 μm, more preferably at most 20 μm. In an embodiment, the first frame 10 has a pore density of at least 30 pores/mm$^2$, preferably at least 40 pores/mm$^2$, more preferably at least 50 pores/mm$^2$, most preferably at least 60 pores/mm$^2$.

Another important property of the first frame 10 is the braid angle, i.e., the angle between the longitudinal direction of the first frame 10 and an individual filament of the first frame 10. The bending flexibility of the braided filaments of the first frame 10 increases as the braid pitch decreases (i.e., as the braid angle increases). This is advantageous in allowing the expandable tube 2 to conform to the tortuous anatomy of blood vessels without exhibiting kinking. A higher braid angle results in improved bending flexibility, smaller pores (permitting higher pore density), and improved longitudinal flexibility. In some embodiments, the braid angle is at least 50°, preferably in the range 50-80°.

Existing stent designs typically only achieve filament counts of 48 filaments, or at most 64 filaments, with pore densities up to 20 or at most 30 pores/mm$^2$. Attempts to increase the filament count further in prior art devices have not maintained compatibility with standard-sized 0.69 mm (0.027 inches) catheters, and have necessitated bespoke and/or larger-sized catheters for deployment.

Dual layer stents have previously been considered. However, existing designs have both layers made from conventional braided filament layers. Some advantages are provided by such a design. However, two braided layers do not have the same improvements in reliability and consistency of expansion that are provided by the present design having one braided frame and one frame of non-overlapping elements.

Furthermore, in a braided frame each filament overlaps with the other filaments at crossing points. This results in a cross-section profile (i.e., an effective thickness of the wall of the frame in the radial direction) of 2*filament diameter. With a dual-layer device having only braided frames, the cross-section profile is further increased to 2*filament diameter of inner frame+2*filament diameter of outer frame. This increased cross-sectional profile is associated with higher thrombogenicity and is undesirable. The present invention can have a reduced cross-sectional profile due to its ability to use thinner filaments and inclusion of the second frame 12 comprising non-overlapping elements. When the expandable tube 2 is positioned in use over the opening to an aneurismal sac in the radially expanded and longitudinally contracted state, the first frame 10 may have a porosity such as to redirect blood flow away from the aneurismal sac and thereby promote thrombus formation in the aneurismal sac. For example, the first frame 10 may have a porosity of at most 90%, preferably at most 80%, more preferably at most 70%, more preferably at most 60%, most preferably at most 50%, in the radially expanded and longitudinally contracted state of the expandable tube. If the porosity of the first frame 10 is alone low enough to redirect blood flow away from an aneurysm, this reduces the design constraints on the second frame 12, allowing it to have a higher porosity.

Figure 9:
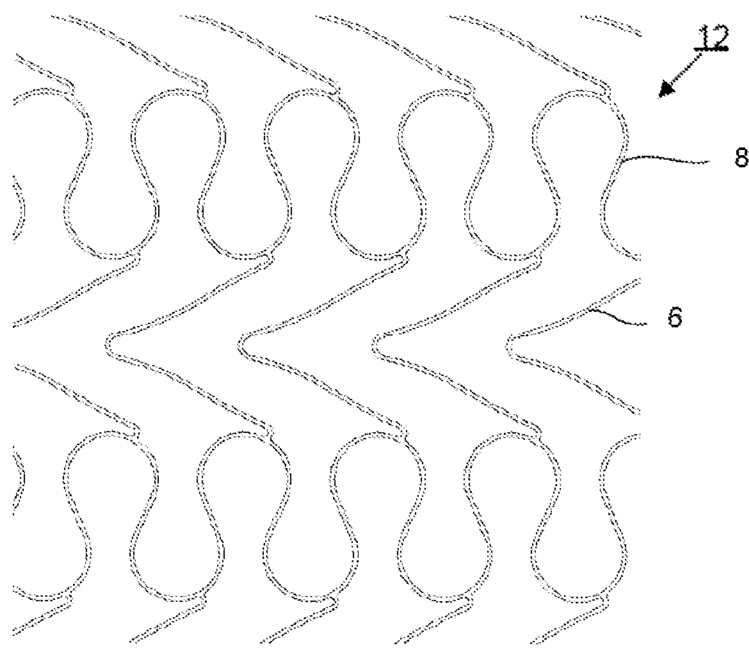
FIG. 9 shows detail of a design of the network of non-overlapping elements of the second frame.

The expandable tube 2 further comprises a second frame 12. The second frame 12 comprises a network of non-overlapping elements, wherein the non-overlapping elements are non-overlapping with respect to each other in the radial direction. This is not the case for the braided filaments of the first frame 10, which overlap with one another in a radial direction. An exemplary design of the network of non-overlapping elements is shown in FIG. 9. By having a network of non-overlapping elements for the second frame 12, the friction between elements that would otherwise be created at the points of overlap is avoided. In turn, this reduces the resistance to the radial expansion of the second frame 12, such that the second frame 12 is able to expand rapidly and consistently on release from a catheter during deployment.

The network of non-overlapping elements is integrally formed, i.e., the non-overlapping elements are connected together to form the network such that there are no material interfaces between any of the elements. This may be achieved by forming the second frame 12 for example by laser cutting a hollow tube, or by other techniques known in the art for manufacturing such structures. Forming the network of non-overlapping elements integrally is preferred because there are no joins between elements that could increase friction, create likely points of failure or similar. However, it is not essential, and in some embodiments the network of non-overlapping elements may be formed by, for example, welding together a plurality of individual elements or similar.

The second frame 12, and specifically the non-overlapping elements, may comprise a shape memory alloy material, preferably nitinol. In some embodiments, the second frame 12 may have a porosity of at least 70%, preferably at least 80%, more preferably at least 90%, most preferably at least 95%. This allows the second frame 12 to have a less dense network of non-overlapping elements, thereby reducing the likelihood of elements interfering with one another during expansion and contraction of the frame, and simplifying the design of the network. It also means that the porosity of the expandable tube 2 as a whole is determined more completely by the first frame 10 alone, thereby allowing the determination of the overall properties of the expandable tube 2 to be simplified. In some embodiments, the second frame 12 may be independently self-expanding. That is, the second frame 12 is configured to self-expand from a radially contracted and longitudinally expanded state to a radially expanded and longitudinally contracted state, even in a state in which the second frame 12 is not connected to the first frame 10.

FIG. 9 shows a close-up of one design of the second frame 12 in which the network of non-overlapping elements comprises a plurality of longitudinally and/or circumferentially deformable elements. Such a plurality of elements allows the second frame 12 to expand and contract longitudinally and/or radially to match the changes in dimension of the first frame 10. In the example of FIG. 9, the network of non-overlapping elements comprises a plurality of longitudinally deformable elements 8 for providing longitudinal expansion and contraction of the second frame 12, and a plurality of circumferentially deformable elements 6 for providing radial expansion and contraction of the second frame 12. The high degree of longitudinal contraction and elongation enabled by the non-overlapping structure of the second frame has a number of advantages. For example, using a small braid pitch (which is preferable in neurovascular applications where high longitudinal flexibility is particularly desirable) results in the first frame 10 longitudinally contracting significantly between the radially contracted and longitudinally expanded state and the radially expanded and longitudinally contracted state (and vice versa). The non-overlapping design of the second frame 12 allows the second frame 12 to match the change in length of the first frame 10 even for short braid pitches.

As mentioned above, an elongation of the expandable tube 2 (or of a frame which forms a part of the expandable tube 2) in the longitudinal direction caused by the switching from the radially expanded and longitudinally contracted state to the radially contracted and longitudinally expanded state is preferably at least 10%. For neurovascular applications, where blood vessels are narrow and tortuous, high longitudinal flexibility is particularly desirable. To provide high longitudinal flexibility in these applications, the elongation of the expandable tube 2 in the longitudinal direction caused by the switching from the radially expanded and longitudinally contracted state to the radially contracted and longitudinally expanded state should be at least 20%, preferably at least 30%.

The network of elements in FIG. 9 is such that the longitudinally deformable elements 8 are configured to be expanded or contracted longitudinally without any substantial change in the shape of the circumferentially deformable elements 6. In an embodiment, the deformation of the longitudinally deformable elements 8 occurs substantially without any deformation of the circumferentially deformable elements 6 for at least a portion of the deformation. Additionally, the network of elements in FIG. 9 is such that the circumferentially deformable elements 6 are configured to be expanded or contracted circumferentially without any substantial change in the shape of the longitudinally deformable elements 8. In an embodiment, the deformation of the circumferentially deformable elements 6 occurs substantially without any deformation of the longitudinally deformable elements 8 for at least a portion of the deformation. This independence in the two types of deformation allows the second frame 12 to follow smoothly and consistently any deformation in the first frame 10.

Figure 10:
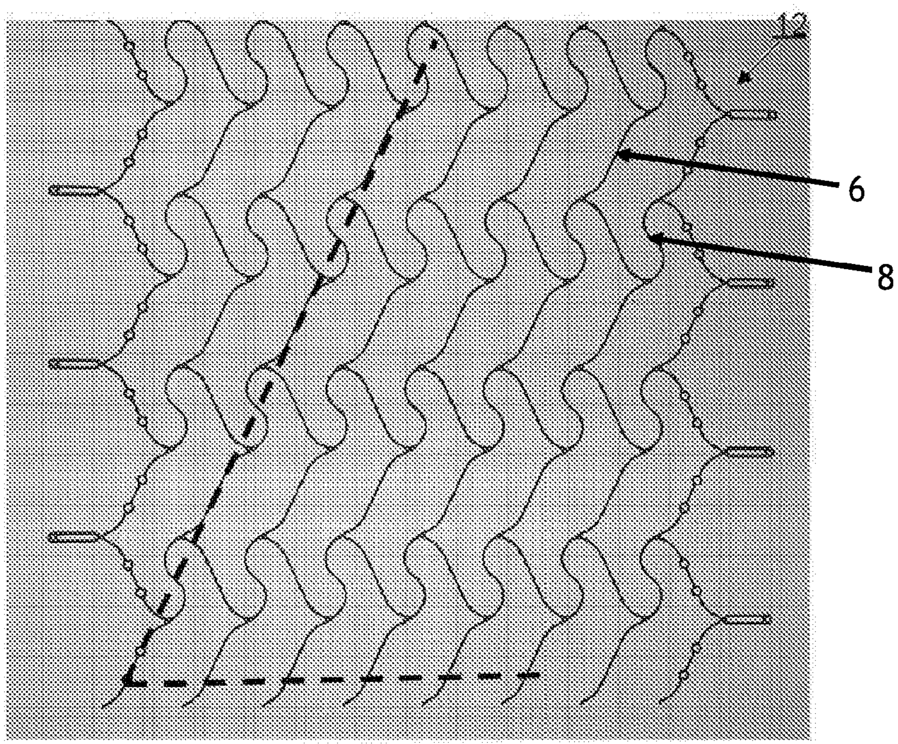
FIG. 10 shows detail of an alternative design of the network of elements of the second frame.

Other designs of the network of non-overlapping elements are possible. FIG. 10 shows a design similar to that of FIG. 9, but in which the circumferentially deformable elements 6 are repeating in the circumferential direction. In other words, the circumferentially deformable elements 6 are connected around the circumference to form a ‘ring’. Each ring is connected by a connecting longitudinally deformable element 8.

In the design of FIG. 9, each circumferentially deformable element 6 joins two longitudinally deformable elements 8 having the same longitudinal position along the expandable tube 2. In contrast, in the design of FIG. 10, each circumferentially deformable element 6 joins two longitudinally deformable elements 8 having different longitudinal positions along the expandable tube 2.

Preferably, as shown by the dashed line in FIG. 10, the angle between the longitudinally deformable elements 8 joined by each circumferentially deformable element 6 matches the braid angle of the braided filaments of the first frame 10.

Figure 11:
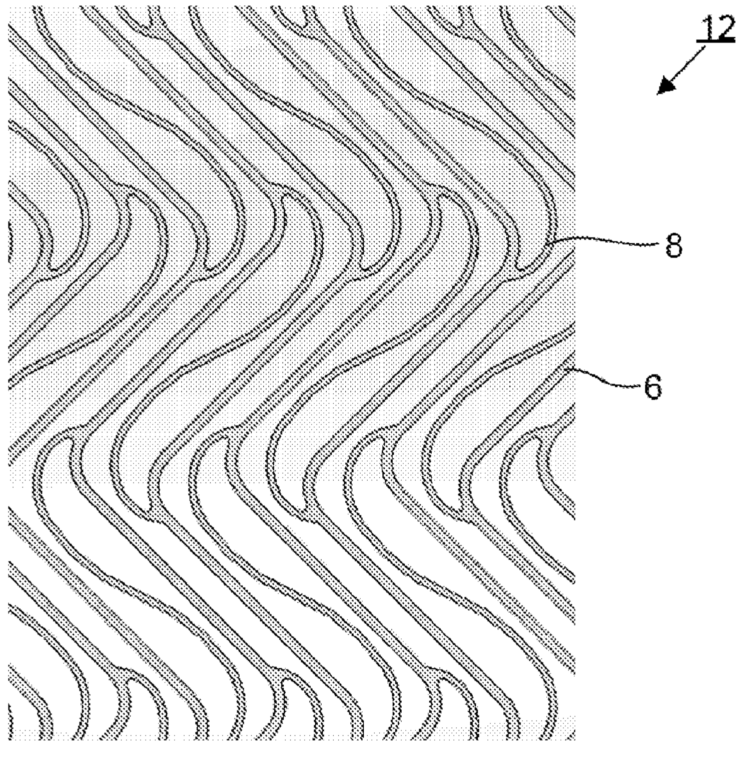
FIG. 11 shows detail of a further alternative design of the network of elements of the second frame.
Figure 12:
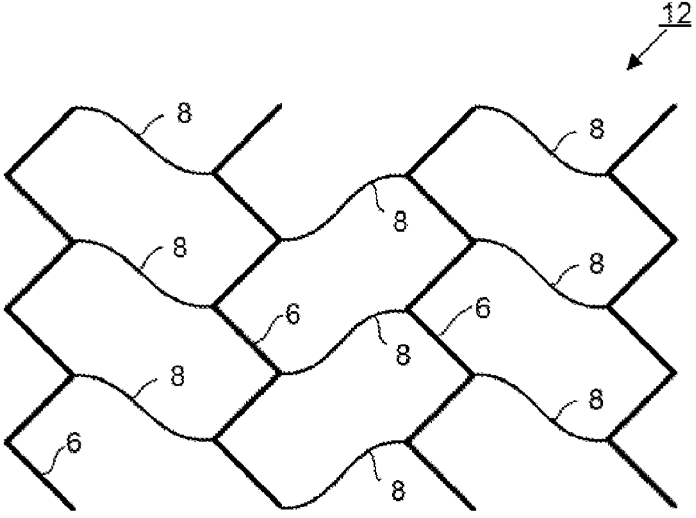
FIG. 12 is a schematic of design of the network of elements of the second frame of FIG. 11.

FIGS. 11 and 12 show another design in which the circumferentially deformable elements 6 form closed rings around the axis of elongation 4 of the expandable tube 2. Each closed ring consists exclusively of the circumferentially deformable elements 6, and each circumferentially deformable element 6 is substantially V-shaped. Each closed ring thus consists of a plurality of Vs connected together at the outer ends of the arms of each V. FIG. 11 shows the network in the radially expanded and longitudinally contracted state of the expandable tube 2, in which the closed rings of circumferentially deformable elements 6 overlap with one another in the longitudinal direction. FIG. 12 shows the network of FIG. 11 in the radially contracted and longitudinally expanded state of the expandable tube 2.

The network of non-overlapping elements has an interconnected structure comprising a plurality of sub-units that repeat in the longitudinal direction. This feature has the advantage that the length of the expandable tube 2 can be easily changed to suit any particular application by adding more sub-units. The sub-units that repeat in the longitudinal direction may themselves comprise a plurality of cells that repeat in the circumferential direction. In this case, the structure of the network of non-overlapping elements may repeat itself in both the longitudinal and circumferential directions. Circumferential repetition of the cells allows the radius of the expandable tube to be easily adjusted depending on the requirements of a particular application.

The second frame 12 overlaps with the first frame 10 in the radial direction. That is, for at least some points along the axis of elongation 4, a line perpendicular to the axis of elongation 4 will pass through both the first frame 10 and the second frame 12. The second frame 12 may overlap with the first frame 10 over at least 50%, preferably at least 60%, more preferably at least 70%, most preferably at least 80%, of the length of the expandable tube 2. In the examples of FIGS. 3 to 5, the first frame 10 and second frame 12 overlap over substantially their entire length. Having substantial overlap between the first frame 10 and second frame 12 ensures that the properties of the expandable tube 2 are the same along the expandable tube 2, such that the behavior of the expandable tube 2 is predictable. In FIG. 3, the second frame 12 is positioned within the first frame 10. However, this is not essential, and in other embodiments, the first frame 10 may be within the second frame 12. If the first frame 10 is within the second frame 12, this may further require that the second frame 12 is connected to the first frame 10 at one or more points along the length of the second frame 12.

The length of the second frame 12 may be at least 50%, preferably at least 60%, more preferably at least 70%, most preferably at least 80%, of the length of the first frame 10. In the examples of FIGS. 3 to 5, the first frame 10 and second frame 12 have substantially the same length. This can also contribute to ensuring the properties of the expandable tube 2 are consistent along the length of the expandable tube 2. The requirements of overlapping and on the relative length of the first frame 10 and second frame 12 will also enable connecting the first frame 10 and second frame 12 together at the ends of the expandable tube 2, which may be preferred in some embodiments.

The second frame 12 is connected to the first frame 10. The connection may be achieved in any suitable way. For example, the second frame 12 may be connected to the first frame 10 by at least one of welding, crimping, an adhesive, or encapsulation. Connecting the first frame 10 and the second frame 12 at a point by encapsulation may be achieved by locally coating the first frame 10 and the second frame 12 together in a contiguous portion of a suitable material, such as a biocompatible polymer (for example PTFE).

In a preferred embodiment, the second frame 12 is connected to the first frame 10 using connecting filaments 16. To facilitate this, the second frame 12 comprises a plurality of filament-receiving apertures 18. One or more connecting filaments 16 are woven into the first frame 10, and each connecting filament 16 passes through one or more of the filament-receiving apertures 18.

The advantage of using connecting filaments 16 is to reduce the profile of the joining between the first and second frames 10, 12 compared to other methods such as crimping or welding, making the surface of the expandable tube 2 more uniform. The filaments also enable joining of a laser-cut structure to a continuous braid (i.e., a braid with a continuous pitch). Further, the filaments 16 are able to deform during expansion and contraction of the expandable tube 2. The use of connecting filaments 16 thereby enables a smooth transition between the radially-contracted and longitudinally-expanded state and the radially-expanded and longitudinally-contracted state, while fixing the first and second frames 10, 12 together at the locations of the filament-receiving apertures 18.

Figure 13:
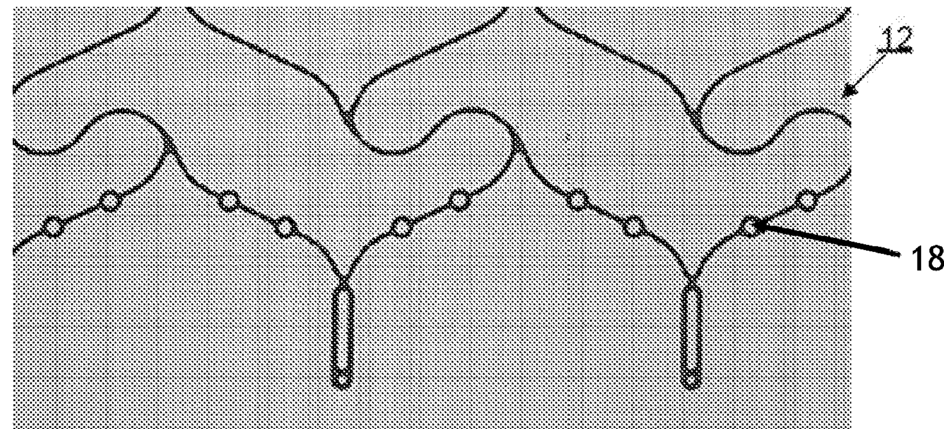
FIG. 13 illustrates apertures at an end of the second frame that can be used for connecting the first and second frames.

FIG. 13 shows an example of a longitudinal end region of the second frame 12 in an embodiment in which the plurality of filament-receiving apertures 18 comprises filament-receiving apertures 18 in a longitudinal end region of the second frame 12. The longitudinal end region may comprise a region within a distance of an end of the expandable tube 2 that is at most 10%, preferably at most 5% of the length of the expandable tube 2. The second frame 12 may comprise filament-receiving apertures 18 in one or both end regions of the expandable tube 2. The filament-receiving apertures 18 in the embodiment of FIG. 13 are located on the longitudinally most distal elements of the network of interconnected elements of the second frame 12. Although not shown, filament-receiving apertures 18 in the embodiment of FIG. 13 are also located on the longitudinally most proximal elements of the network of interconnected elements of the second frame 12.

Figure 14:
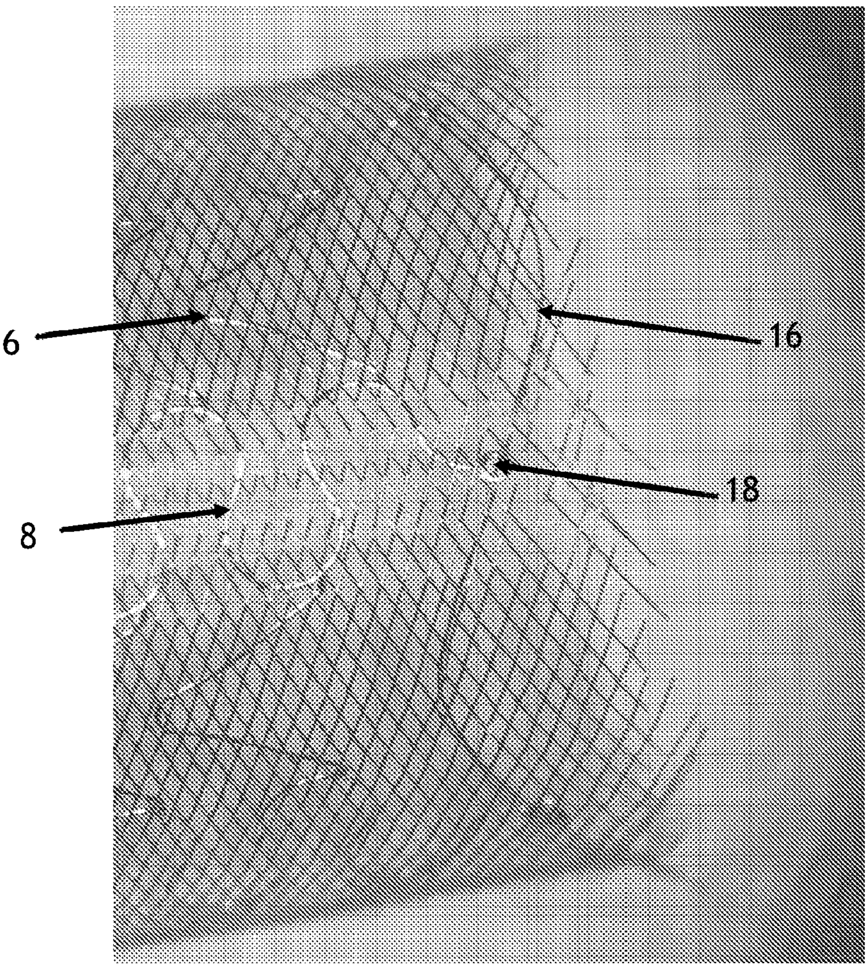
FIG. 14 shows detail of the use of apertures and a joining filament to connect the first and second frames.
Figure 15:
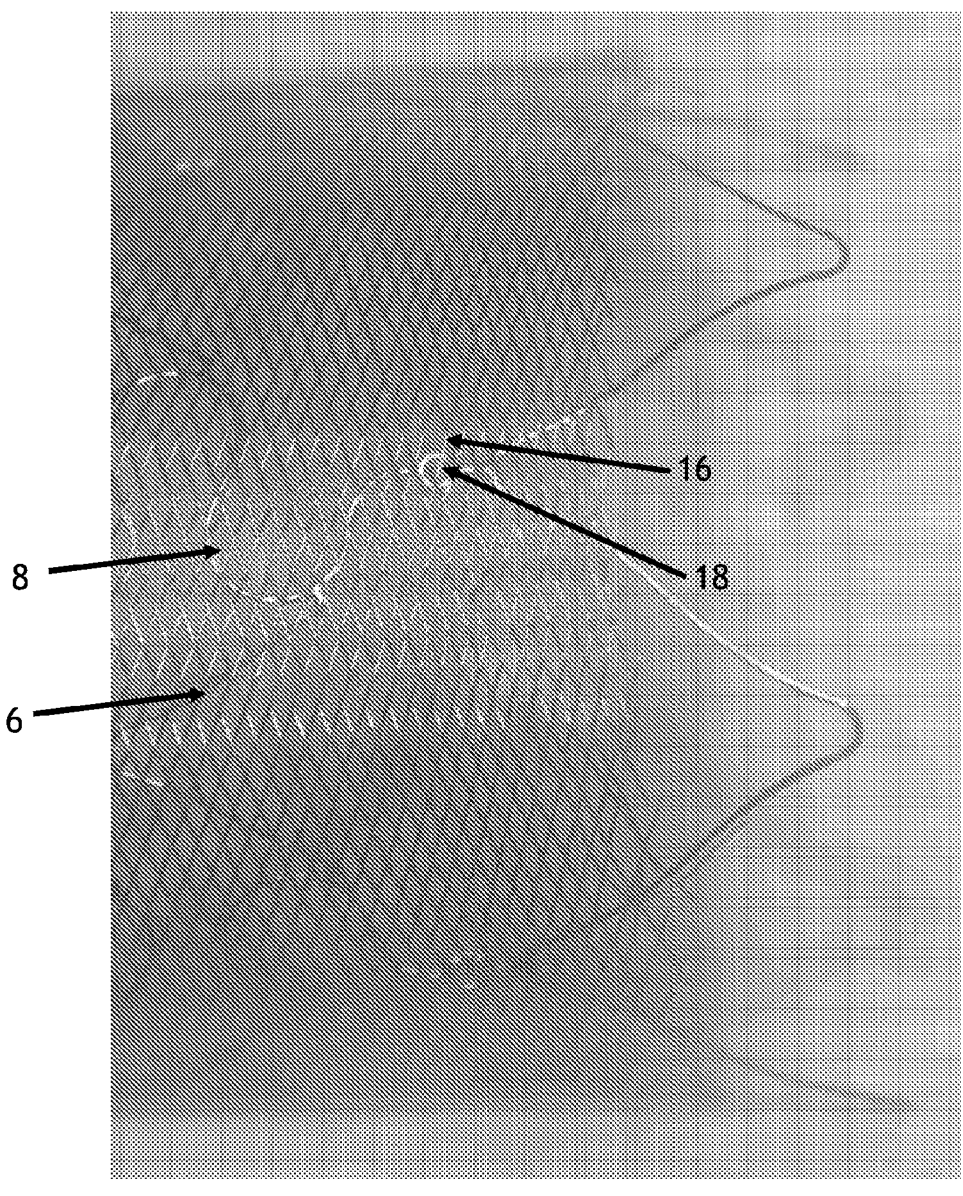
FIG. 15 shows detail of an alternative design to that of FIG. 14 in which the filaments of the first frame are used as the joining filaments connecting the first and second frames.

As shown in FIG. 14 and FIG. 15, one or more connecting filaments 16 are woven into the first frame 10, and each connecting filament 16 passes through one or more of the filament-receiving apertures 18.

In the example of FIG. 13, the second frame 12 comprises two filament-receiving apertures 18 on the same element of the second frame 12. In this case, the angle between a line between the filament-receiving apertures 18 on the same element and the longitudinal axis 4 of the expandable tube 2 is preferably the same as the braid angle of the braided filaments of the first frame 10. Thereby, a connecting filament 16 passing through the filament-receiving apertures 18 on the same element of the second frame 12 will run parallel to the filaments of the first frame 10. This facilitates the weaving of the connecting filaments 16 into the first frame 10.

The connecting filaments 16 are woven into the first frame 10. In this way, the connecting filaments 16 alternately pass over and under the filaments of the first frame 10 (under and over being interpreted as respectively closer to and further from the axis of the expandable tube 2 in the radial direction). Other arrangements are also possible. For example, the connecting filaments 16 may pass alternately under and over pairs of filaments of the first frame 10, or larger sets of filaments, such as three, four, or more filaments. Passing under and over multiple filaments of the first frame 10 may be advantageous in reducing assembly time. The arrangement of the connecting filaments 16 may match the arrangement of the filaments of the first frame 10, or may be different. For example, if the connecting filaments 16 have a larger diameter than the filaments of the first frame 10, it may be desirable for the connecting filaments 16 to pass over and under larger sets of filaments of the first frame 10 than do the filaments of the first frame 10 themselves.

In embodiments where the plurality of filament-receiving apertures 18 comprises filament-receiving apertures 18 in a longitudinal end region of the second frame 12, the connecting filaments 16 may be woven into the first frame 10 around a circumference of the first frame 10. An example of such an embodiment is shown in FIG. 14. In this case, the connecting filaments 16 bend at regular intervals to alternately follow the filaments of the right-handed helices and left-handed helices of the first frame 10. To facilitate this, the connecting filaments 16 may be bent to the desired shape before being woven into the first frame 10. This helps to retain the bends at the correct position and angle after the connecting filament 16 has been woven into the first frame 10. Where the connecting filaments 16 comprise wire, the wire may be shape set to achieve the bending at the desired positions to facilitate the transition between radially contracted and radially expanded configurations. Embodiments where the connecting filaments 16 are woven into the first frame 10 around a circumference of the first frame 10 may also improve the expansion properties of the expandable frame 2, as the connecting filaments 16 at the ends of the expandable tube 2 can contribute to encouraging radial expansion when the expandable tube 2 is deployed from a catheter.

The connecting filaments 16 may comprise the same material and/or have the same diameter as the filaments of the first frame 10. In an embodiment, the connecting filaments 16 comprise filaments of the first frame 10. Such an embodiment is shown in FIG. 15. In such embodiments, joining the first and second frames 10, 12 together may comprise unbraiding one or more filaments of the first frame 10 to use as the connecting filaments 16. The connecting filaments 16 are then passed through the apertures 18 in the second frame 12 and woven back into the other braided filaments of the first frame 10.

Alternatively, the connecting filaments 16 may have a different diameter or be made of a different material to the filaments of the first frame 10. The connecting filaments 16 may comprise nitinol wire. The connecting filaments 16 may comprise materials typically used for medical sutures. In this embodiment, two ends of the suture can be tied to secure the two frames together.

Figure 16:
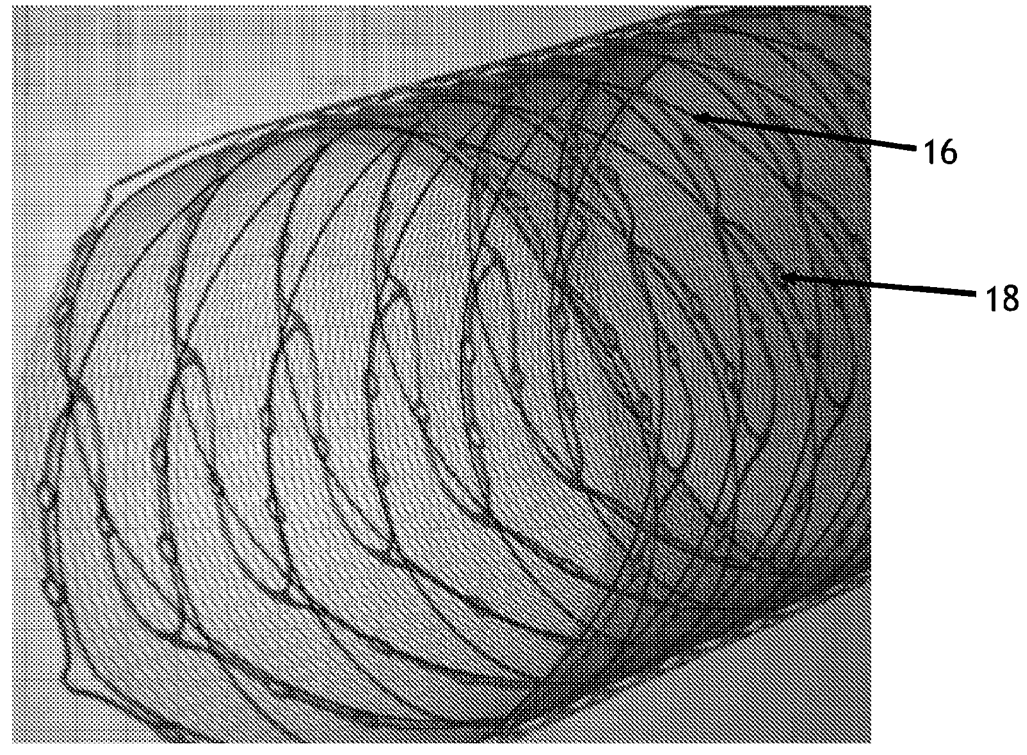
FIG. 16 shows an embodiment in which apertures are present along the entire length of the second frame.

In some embodiments, the plurality of filament-receiving apertures 18 comprises filament-receiving apertures 18 spaced along the length of the second frame 12. An example of such an embodiment is shown in FIG. 16. The filament-receiving apertures 18 may be spaced at intervals along the length of the second frame 12, preferably equal intervals. The spacing between filament-receiving apertures 18 may be at most 50% of the length of the expandable tube 2, preferably at most 25%, more preferably at most 10%. In some embodiments, each longitudinally-expandable element 8 of the second frame 12 comprises a filament-receiving aperture.

Including filament-receiving apertures 18 spaced along the second frame 12 improves the attachment of the first and second frames 10, 12 to one another, reducing the chance of the two frames separating. This also means that the connecting filaments 16 do not need to be bent in the manner shown in FIG. 14, but can instead follow the helical path of the braided filaments of the first frame 10 along the entire length of the first frame 10. This is advantageous because the connecting filaments 16 are under less tension than when bent. As shown in FIG. 16, multiple connecting filaments 16 may be provided, following both the right-handed and left-handed helices of the braided filaments of the first frame 10.

Preferably, the apertures 18 are arranged such that each connecting filament 16 follows the braid angle of the braided filaments of the first frame 10 as the connecting filament 16 passes through the apertures 18. To achieve this, where multiple filament-receiving apertures 18 are provided on the same element of the second frame 12, the angle between a line between the filament-receiving apertures 18 on the same element and the longitudinal axis 4 of the expandable tube 2 is preferably the same as the braid angle of the braided filaments of the first frame 10. This also reduces unnecessary bending of the connecting filaments 16 and reduces tension in the connecting filaments 16.

Figure 17:
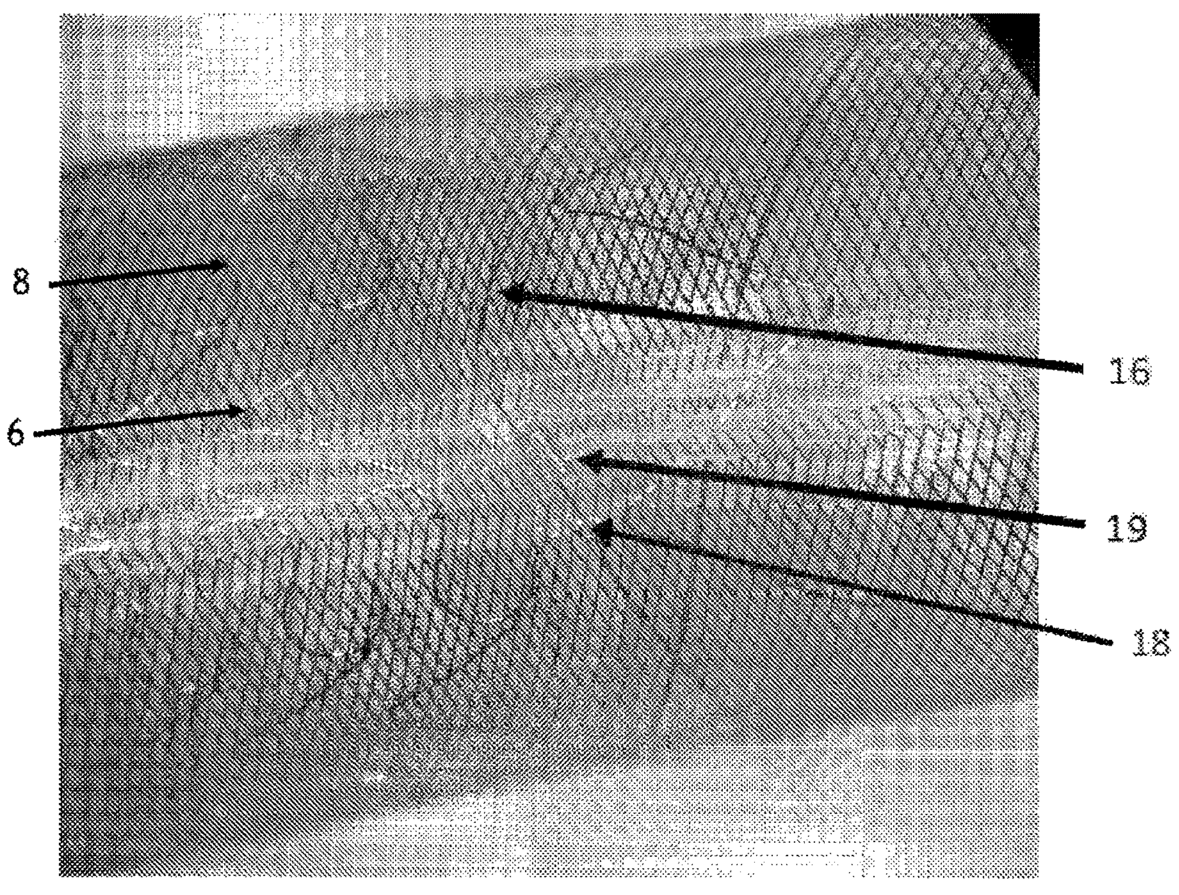
FIG. 17 shows the addition of a radiopaque marker to a joining filament.

The connecting filaments 16 may contribute to improving the visibility of the expandable tube 2 during deployment. For example, the connecting filaments 16 may comprise a radiopaque material. Alternatively, as shown in FIG. 17, one or more radiopaque markers may be attached to one or more of the connecting filaments 16.

The connection should be achieved in a way which is biocompatible, so that it does not affect the ability of the expandable tube 2 to be inserted into the body of a human or animal. The expandable tube 2 may be left in the body for an extended time after deployment, typically indefinitely. It is therefore also important that any materials used for connection are biocompatible.

The second frame 12 may be connected to the first frame 10 at least at one end of the second frame 12. Connection at the end of the second frame 12 may be convenient because the ends of elements of the second frame 12 can be joined to the first frame 10, for example to ends of the filaments of the first frame 10. The second frame 12 may be further connected to the first frame 10 at one or more points along the length of the second frame 12. Joining the first frame 10 and second frame 12 at further points along the length of the second frame 12 will contribute to preventing the first frame 10 and second frame 12 from separating at any point along the length of the expandable tube 2, or buckling or creasing. This is particularly relevant when the expandable tube 2 is expanding or contracting. Separation of the first frame 10 and second frame 12 could cause incorrect deployment of or damage to the expandable tube 2. However, joining at multiple points along the length of the expandable tube 2 would increase the complexity of manufacture of the expandable tube 2, and so may not be preferred in all embodiments.

The connection between the first frame 10 and the second frame 12 may also be designed to reduce the likelihood of damaging a blood vessel into which the expandable tube 2 is deployed. For example, in FIG. 5, the ends of the braided filaments of the first frame 10 and the elements of the second frame 12 are contained in a terminating element 14. The terminating element 14 is configured to reduce the likelihood of damage to the interior of a blood vessel, for example by preventing any sharp points at the ends of filaments or other sharp surfaces from coming into contact with the interior walls of a blood vessel. The terminating element 14 itself may have smooth and/or curved surfaces to prevent any damage to the blood vessel.

In some embodiments, the second frame 12 is configured to drive the expandable tube 2 from the radially contracted and longitudinally expanded state to the radially expanded and longitudinally contracted state. As mentioned above, a problem with prior art expandable tubes composed only of braided filaments is that they do not always expand uniformly or reliably due to friction between the filaments. By including the second frame 12 which is configured to drive the expandable tube 2 to expand radially and contract longitudinally, the behavior of the expandable tube 2 can be made more reliable and consistent. In some embodiments, the second frame 12 is configured to drive the expandable tube 2 from the radially contracted and longitudinally expanded state to the radially expanded and longitudinally contracted state by exerting a force on the first frame 10 in a radial direction. Consistent radial expansion is important such that the expandable tube 2 expands to its final size and engages with the interior walls of the blood vessel in which it is deployed. In other embodiments, the second frame 12 may drive the expandable tube 2 from the radially contracted and longitudinally expanded state to the radially expanded and longitudinally contracted state by exerting a force on the first frame 10 in a longitudinal direction. However, this is not generally preferred, because the drive to expand the expandable tube 2 radially is then only indirect, and may not have as great an improvement in the consistency of radial expansion on deployment.

In an embodiment, a radius of the second frame 12 in an unconstrained state in which the second frame 12 is not connected to the first frame 10 and the second frame 12 is radially expanded and longitudinally contracted is greater than a radius of the first frame 10 in an unconstrained state in which the first frame 10 is not connected to the second frame 12 and the first frame 10 is radially expanded and longitudinally contracted. Both the first frame 10 and second frame 12 are configured to urge themselves towards a radially expanded and longitudinally contracted state, and will have a maximum radius that they attain when unconstrained. When the first frame 10 and second frame 12 are connected together to form the expandable tube, their respective maximum radii in the radially expanded and longitudinally contracted state of the expandable tube 2 will be constrained to be the same, i.e., the smaller of the radii of the first frame 10 and second frame 12 in their unconstrained states. By designing the second frame 12 such that its radius in an unconstrained state is larger than that of the first frame 10 in an unconstrained state, the second frame 12 will drive the first frame 10 to expand to its maximum radius and minimize the risk of radial separation between the two frames, particularly when deployed in tortuous anatomy. This will improve the consistency of the radial expansion of the first frame 10, which comprises braided filaments. This feature also means that fewer fixation points are required to join the two frames together securely.

In some embodiments, at least one of the first frame 10 and the second frame 12 may be provided with a hydrophilic coating and/or an anti-thrombotic coating.

This multi-layered expandable tube 2 design comprising a first frame 10 and a second frame 12 relies on the first frame 10 and second frame 12 longitudinally expanding and contracting, and radially expanding and contracting, together with each other. The extent of longitudinal and radial expansion and contraction of the expandable tube 2 is determined primarily by the braided structure of the first frame 10, and the second frame 12, for example containing longitudinally and circumferentially independent elements, adapts to the longitudinal and radial movement of the braided structure.

In an embodiment, a first elongation ratio of the first frame 10 is within 25%, preferably within 15%, more preferably within 10%, most preferably within 5%, of a second elongation ratio of the second frame 12. The first elongation ratio of the first frame 10 is a ratio between an unconstrained length of the first frame 10 and the length of the first frame 10 in the radially contracted and longitudinally expanded state. The unconstrained length of the first frame is the length of the first frame 10 in an unconstrained state in which the first frame 10 is not connected to the second frame 12 and the first frame 10 is radially expanded and longitudinally contracted. The second elongation ratio is a ratio between an unconstrained length of the second frame 12 and the length of the second frame 12 in the radially contracted and longitudinally expanded state. The unconstrained length of the second frame 12 is the length of the second frame 12 in an unconstrained state in which the second frame 12 is not connected to the first frame 10 and the second frame 12 is radially expanded and longitudinally contracted. The radially contracted and longitudinally expanded state referred to is that of the first frame 10 or second frame 12 when it is part of the expandable tube 2 (i.e., connected to the second frame 12) and the expandable tube 2 is in its radially contracted and longitudinally expanded state. This may be, for example, when the expandable tube 2 is inside a catheter ready to be deployed. Previous designs of expandable tubes comprising braided filaments have included expansion rings at one or both ends of the expandable tube to promote proper deployment of the end of the braided tube. However, increasing the length of the expansion rings relative to the braided stent to promote proper deployment over the full length is challenging because the expansion characteristic of the two types of frame are different. Matching the first elongation ratio and the second elongation ratio ensures that the chance of buckling of the first frame 10 or the second frame 12, or separation of the first frame 10 and second frame 12, is reduced. This further permits the second frame to be made longer in relation to the first frame, and further improve the consistency of deployment of the expandable tube.

To define the dimensional inputs for designing the second frame 12, it is necessary to determine the elongation ratio of the first frame 10 analytically. Two methods are outlined below for determining the first elongation ratio of the first frame 10, and the elements of the second frame can be designed so that the second elongation ratio matches the first elongation ratio to the required extent. The first method outlines a detailed approach by determining length and height change of a single pore of the first frame 10 between the radially expanded and longitudinally contracted state and the radially contracted and longitudinally expanded state. A pore is a single space defined by neighboring filaments in the first frame 10, as illustrated schematically in FIG. 18. The radially contracted and longitudinally expanded state may also be referred to as the loaded state, since this is the state of the expandable tube 2 when it is loaded into a catheter prior to deployment into a blood vessel. The second method offers a more simplistic approach to estimate the total length change of the first frame 10 between the radially expanded and longitudinally contracted state and the radially contracted and longitudinally expanded state.

Figure 19:
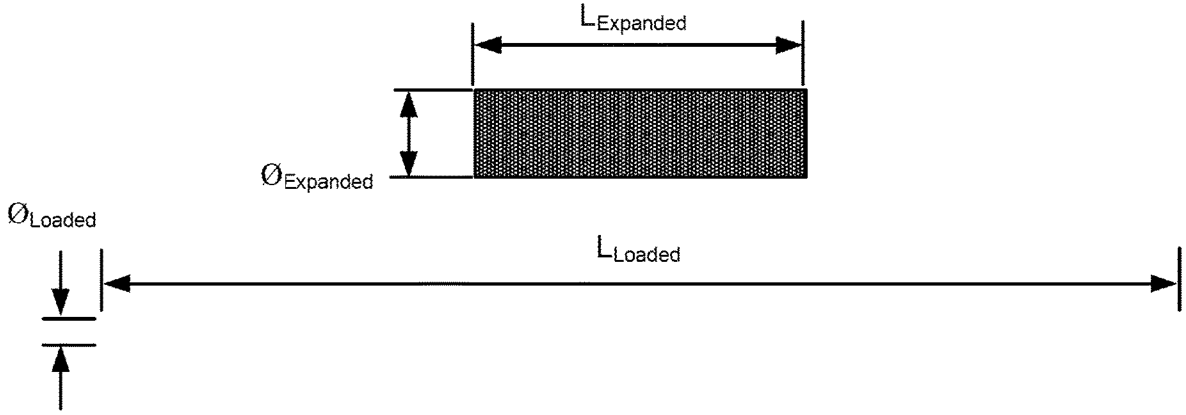
FIG. 19 illustrates the dimensions of the expandable tube in the radially expanded and longitudinally contracted state, and the radially contracted and longitudinally expanded state.

The first method starts with the diameter $\varnothing_{expanded}$ of the expandable tube 2 in the radially expanded and longitudinally contracted state, as seen in FIG. 19, and the braid angle, $\theta_{braid}$. The braid angle $\theta_{braid}$ is the angle between the longitudinal direction of the first frame 10 and an individual filament of the first frame 10. This angle will change depending on whether the expandable tube 2 is in the radially expanded and longitudinally contracted state, or the radially contracted and longitudinally expanded state. The circumference of the expandable tube 2 C can then be calculated using Eq. 1.

$$C = \pi \varnothing_{expanded} \quad \text{Eq. 1}$$

The circumferential distance, $D_c$, between the filaments in the first frame 10 can be calculated using Eq. 2.

$$D_c = \frac{N_{wire}}{C} \quad \text{Eq. 2}$$

where $N_{wire}$ is the number of filaments in the first frame 10.

Figure 18:
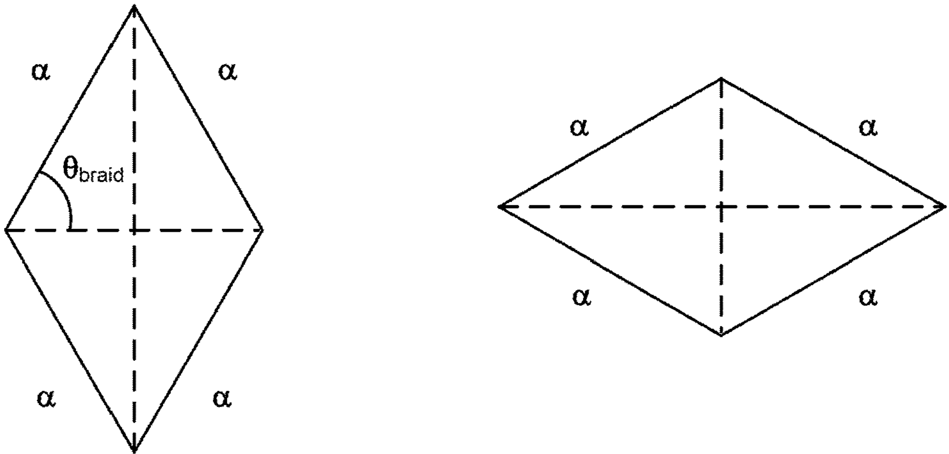
FIG. 18 illustrates the change in shape of spaces between the braided filaments in the first frame between the radially expanded and longitudinally contracted, and radially contracted and longitudinally expanded states.

The pores of the first frame 10 have a rhombus shape with the length of each side of the pore remaining constant as the diameter of the first frame 10 reduces, resulting in a decrease in pore height and an increase in pore length, as shown in FIG. 18.

The longitudinal length of a pore, $L_{pore}$, is calculated using Eq. 3.

$$L_{pore} = 2\alpha \sin(90° - \theta_{braid}) \quad \text{Eq. 3}$$

The circumferential height of a pore, $H_{pore}$, can be calculated using Eq. 4.

$$H_{pore} = 2\alpha \cos(90° - \theta_{braid}) \quad \text{Eq. 4}$$

The total number of pores around the circumference, $N_c$, can be calculated using Eq. 5.

$$N_c = \frac{C}{H_{pore}} \quad \text{Eq. 5}$$

The total number of pores in a single row along the length of the first frame 10, $N_h$, can be calculated using Eq. 6.

$$N_h = \frac{L_{expanded}}{H_{pore}} \quad \text{Eq. 6}$$

where $L_{expanded}$ is the length of the first frame 10 in the radially expanded and longitudinally contracted state, as seen in FIG. 19. Using the number of pores around the circumference, $N_c$, the circumferential height of each pore in the loaded state, $H_{loaded}$, can be calculated using Eq. 7.

$$H_{loaded} = \frac{D_{catheter}\pi}{N_c} \quad \text{Eq. 7}$$

where $D_{catheter}$ is the internal diameter that the expandable tube 2 must be reduced to for deployment, e.g., the internal diameter of the delivery catheter. The braid angle in the loaded state $\theta_{loaded}$ can be calculated using Eq. 8.

$$\theta_{loaded} = \sin^{-1}\left(\frac{0.5H_{loaded}}{a}\right) \quad \text{Eq. 8}$$

Subsequently, the longitudinal length of each pore in the loaded state $L_{loaded\ pore}$ can be calculated using Eq. 9.

$$L_{loaded\ pore} = 2a\cos(90° - \theta_{loaded}) \qquad \text{Eq. 9}$$

The length of the first frame 10 in the loaded state, $L_{loaded}$, as seen in FIG. 19, can then be calculated using Eq. 10.

$$L_{loaded} = N_h L_{loaded\ pore} \qquad \text{Eq. 10}$$

Finally, the first elongation ratio, E, can be determined using Eq. 11.

$$\epsilon = \frac{L_{loaded}}{L_{expanded}} \qquad \text{Eq. 11}$$

The second method is a more simplistic approach applied to estimate the elongation ratio of the first frame 10 assuming the length of an individual filament in the first frame 10 is equal to the length of the first frame 10 in the loaded state.

The first step is to calculate the pitch P of a helix with a known braid angle, $\theta_{braid}$, and circumference C using Eq. 12.

$$P = \frac{C}{\tan(\theta_{braid})} \qquad \text{Eq. 12}$$

The number of turns $N_{turns}$ per filament in the first frame 10 can be determined for a defined length in the radially expanded and longitudinally contracted state, $L_{expanded}$, using Eq. 13.

$$N_{turns} = \frac{L_{expanded}}{P} \qquad \text{Eq. 13}$$

Assuming the length of the filaments in the first frame 10 is equal to the length of the first frame in the loaded state, Eq. 14 can be applied.

$$L_{loaded} = \sqrt{(\pi \phi_{expanded} N_{turns})^2 + L_{expanded}^2} \qquad \text{Eqn. 14}$$

As for the first method, Eq. 11 can be used to determine the first elongation ratio. Additionally, the number of cells, N cells, can be determined by applying Eq. 15.

$$N_{cells} = \frac{L_{expanded}}{L_{cell}} \qquad \text{Eq. 15}$$

It should be noted that the number of cells in the second frame 12 should be a whole number, and this must be taken into account when choosing the parameters of the first frame 10 to ensure that the lengths remain the same for the first frame 10 and second frame 12 in both the radially expanded and longitudinally contracted state and the radially contracted and longitudinally expanded state.

Figure 20:
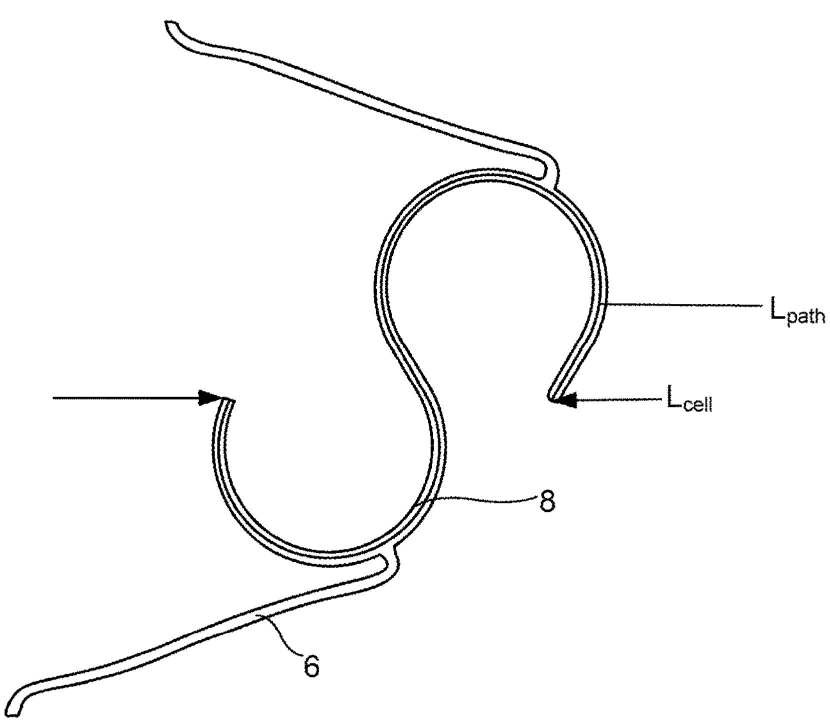
FIG. 20 illustrates the path length along a longitudinally deformable element, and the length of a sub-unit of the network of non-overlapping elements in the design of the network of FIG. 9.

Once the first elongation ratio of the first frame 10 is known, it is possible to define the geometry of an individual cell of the second frame 12, as shown in FIG. 20. This is done for embodiments where the sub-units of the network of non-overlapping elements of the second frame 12 that repeat in the longitudinal direction themselves comprise a plurality of cells that repeat in the circumferential direction (as described above).

In such an embodiment, the network of non-overlapping elements comprises a plurality of longitudinally deformable elements 8 for providing longitudinal expansion and contraction of the second frame. Each sub-unit of the network of non-overlapping elements has a first length in the longitudinal direction in the unconstrained state in which the second frame 12 is not connected to the first frame 10 and the second frame 12 is radially expanded and longitudinally contracted state.

The longitudinally deformable elements 8 are designed to match the elongation of the first frame 10 by ensuring that the path length along each longitudinally deformable element 8, $L_{path}$, and the first length (i.e. the length of each cell in the radially expanded and longitudinally contracted state), $L_{cell}$, are in proportion to the first elongation ratio of the first frame 10. In an embodiment, a ratio between the first length and the path length along each longitudinally deformable element 8 is within 25%, preferably within 15%, more preferably within 10%, most preferably within 5%, of the first elongation ratio.

Figure 21:
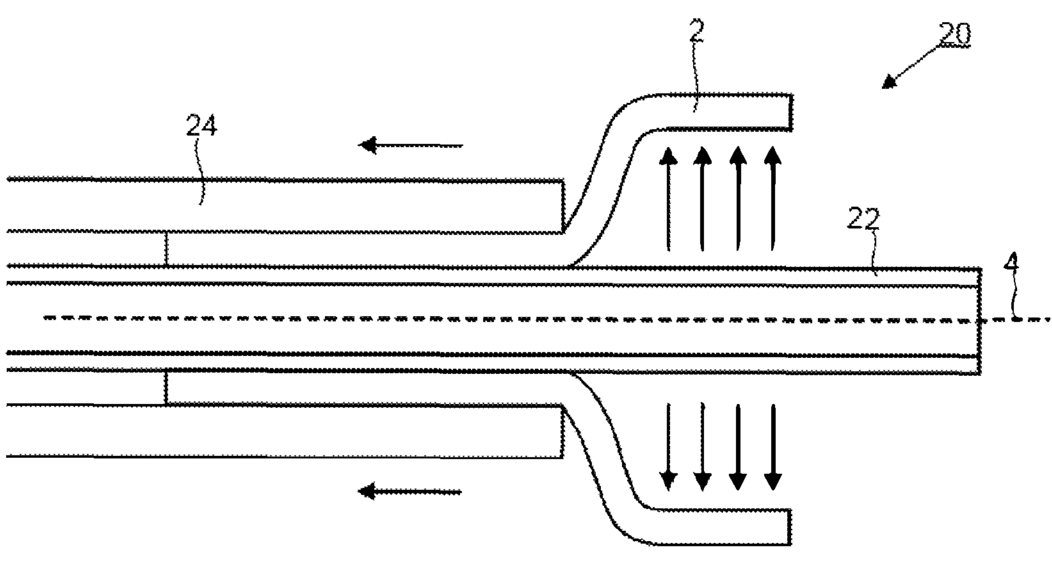
FIG. 21 is a schematic of deployment of an expandable tube from a catheter.

The expandable tube 2 may be configured for use in a delivery system 20 such as that shown in FIG. 21. The delivery system 20 comprises a tubular member 24, also referred to as a catheter, and an elongate body 22, also referred to as a guide wire. The elongate body 22 is positioned within the tubular member 24, and the expandable tube 2 is positioned between the tubular member 24 and the elongate body 22. The expandable tube 2 engages inwardly with the elongate body 22 and outwardly with the tubular member 24. The delivery system 20 is positioned at an appropriate location near an aneurysm in a blood vessel, and the elongate body 22 is extended beyond the end of the tubular member 24. The longitudinal engagement forces between the elongate body 22 and the expandable tube 2 and between the expandable tube 2 and the tubular member 24 are such that the expandable tube is also moved longitudinally and deployed out of the tubular member 24. The expandable tube 2 expands radially and contracts longitudinally, thereby disengaging from the elongate body 22 and deploying into the blood vessel. Once the expandable tube 2 is fully deployed out of the tubular member 24, the delivery system 20 can be withdrawn from the blood vessel, leaving the expandable tube 2 in place.

Although this type of delivery system is preferred, the expandable tube 2 may also be used with other suitable types of conventional delivery system. For example, the expandable tube 2 may be deployed using a delivery system which does not comprise an elongate body that engages outwardly with the expandable tube 2. The expandable tube 2 may be deployed using a delivery system that pushes the expandable tube 2 from the proximal end. This type of delivery system is often not suitable for expandable tubes comprising a network of non-overlapping elements. This is particularly true when those expandable tubes are designed to have high longitudinal flexibility, e.g., for use in neurovascular applications, and therefore have poor longitudinal stiffness. However, the hybrid design of the present expandable tube 2 allows deployment using this type of delivery system because of the higher filament density afforded by the first frame 10.

I claim:

1. An expandable tube for deployment within a blood vessel, the expandable tube being reversibly switchable from a radially contracted and longitudinally expanded state to a radially expanded and longitudinally contracted state, the expandable tube comprising:

a first frame comprising braided filament; and a second frame connected to the first frame and overlapping with the first frame in a radial direction, the second frame comprising a network of non-overlapping elements, the non-overlapping elements being non-overlapping with respect to each other in the radial direction, wherein;

the network of non-overlapping elements has an interconnected structure comprising a plurality of sub-units that repeat in a longitudinal direction; and the second frame is configured to drive the expandable tube from the radially contracted and longitudinally expanded state to the radially expanded and longitudinally contracted state.

2. The expandable tube of claim 1, wherein the network of non-overlapping elements comprises a plurality of longitudinally and/or circumferentially deformable elements.

3. The expandable tube of claim 2, wherein the network of non-overlapping elements comprises a plurality of longitudinally deformable elements for providing longitudinal expansion and contraction of the second frame, and a plurality of circumferentially deformable elements for providing radial expansion and contraction of the second frame.

4. The expandable tube of claim 3, wherein the longitudinally deformable elements are configured to be expanded or contracted longitudinally without any substantial change in the shape of the circumferentially deformable elements.

5. The expandable tube of claim 3, wherein the circumferentially deformable elements are configured to be expanded or contracted circumferentially without any substantial change in the shape of the longitudinally deformable elements.

6. The expandable tube of claim 1, wherein the second frame is configured to drive the expandable tube from the radially contracted and longitudinally expanded state to the radially expanded and longitudinally contracted state by exerting a force on the first frame in the radial direction.

7. The expandable tube of claim 1, wherein the network of non-overlapping elements is integrally formed.

8. The expandable tube of claim 1, wherein one or more of:

i) the second frame comprises a shape memory alloy material;

ii) the second frame has a porosity of at least 70%;

iii) a length of the second frame is at least 50% of a length of the first frame;

iv) the second frame overlaps with the first frame over at least 50% of a length of the expandable tube.

9. The expandable tube of claim 1, wherein the second frame is connected to the first frame at least at one end of the second frame.

10. The expandable tube of claim 9, wherein the second frame is further connected to the first frame at one or more points along the length of a second frame.

11. The expandable frame of claim 1, wherein the second frame is connected to the first frame by at least one of welding, crimping, an adhesive, or encapsulation.

12. The expandable tube of claim 1, wherein:

the second frame comprises a plurality of filament-receiving apertures;

one or more connecting filaments are woven into the first frame; and each connecting filament passes through one or more of the filament-receiving apertures.

13. The expandable tube of claim 12, wherein the one or more connecting filaments comprise filaments of the first frame.

14. The expandable tube of claim 12, wherein one or more radiopaque markers are attached to one or more of the one or more connecting filaments.

15. The expandable tube of claim 12, wherein the plurality of filament- receiving apertures comprises one or more of i) filament-receiving apertures in a longitudinal end region of the second frame, and ii) filament-receiving apertures spaced along a length of the second frame.

16. The expandable tube of claim 1, wherein the second frame is positioned within the first frame.

17. The expandable tube of claim 1, wherein a radius of the second frame in an unconstrained state in which the second frame is not connected to the first frame and the second frame is radially expanded and longitudinally contracted is greater than a radius of the first frame in an unconstrained state in which the first frame is not connected to the second frame and the first frame is radially expanded and longitudinally contracted.

18. The expandable tube of claim 1, wherein a first elongation ratio of the first frame is within 25% of a second elongation ratio of the second frame, the first elongation ratio being a ratio between a length of the first frame in an unconstrained state in which the first frame is not connected to the second frame and the first frame is radially expanded and longitudinally contracted and the length of the first frame in the radially contracted and longitudinally expanded state, and the second elongation ratio being a ratio between a length of the first frame when the expandable tube is in an unconstrained state in which the second frame is not connected to the first frame and the second frame is radially expanded and longitudinally contracted and a length of the second frame when the expandable tube is in the radially contracted and longitudinally expanded state.

19. The expandable tube of claim 18, wherein:

the network of non-overlapping elements comprises a plurality of longitudinally deformable elements for providing longitudinal expansion and contraction of the second frame;

each sub-unit of the network of non-overlapping elements has a first length in the longitudinal direction in the unconstrained state in which the second frame is not connected to the first frame and the second frame is radially expanded and longitudinally contracted state; and a ratio between the first length and a path length along each longitudinally deformable element is within 25% of the first elongation ratio.

20. The expandable tube of claim 1, wherein one or more of:

i) the first frame comprises a shape memory alloy material;

ii) the first frame has a porosity of at most 90% in the radially expanded and longitudinally contracted state of the expandable tube;

iii) the first frame comprises at least 48 filaments;
iv) the filaments of the first frame have a diameter of at most 30 μm;
v) the first frame has a pore density of at least 30 pores/$mm^2$;
vi) the first frame has a braid angle of at least 50°.

21. The expandable tube of claim 1, wherein when the expandable tube is positioned in use over an opening to an aneurismal sac in the radially expanded and longitudinally contracted state, the first frame has a porosity such as to redirect blood flow away from the aneurismal sac and thereby promote thrombus formation in the aneurismal sac.

22. The expandable tube of claim 1, wherein in the radially contracted and longitudinally expanded state, the expandable tube has a maximum dimension in the radial direction that is at least 30% smaller than a maximum dimension in the radial direction of the expandable tube in the radially expanded and longitudinally contracted state.

23. The expandable tube of claim 1, wherein an elongation of the expandable tube in the longitudinal direction caused by the switching from the radially expanded and longitudinally contracted state to the radially contracted and longitudinally expanded state is at least 10%.

24. The expandable tube of claim 1, wherein, in the radially contracted and longitudinally expanded state, a maximum dimension in the radial direction of the expandable tube is such that the expandable tube can be inserted into a catheter having an inner diameter of at most 1.0 mm.

* * * * *